(12) United States Patent
Ait-Haddou et al.

(10) Patent No.: US 8,802,448 B2
(45) Date of Patent: Aug. 12, 2014

(54) MIXED MODE LIGANDS

(75) Inventors: Hassan Ait-Haddou, Melville, NY (US); Frank Onyemauwa, Pace, FL (US); Jonathan Haigh, Sadberge (GB); Samuel Nochumson, Pensacola, FL (US)

(73) Assignee: Pall Corporation, Port Washington, NY (US)

( * ) Notice: Subject to any disclaimer, the term of this patent is extended or adjusted under 35 U.S.C. 154(b) by 0 days.

(21) Appl. No.: 13/555,484

(22) Filed: Jul. 23, 2012

(65) Prior Publication Data

US 2013/0030154 A1   Jan. 31, 2013

Related U.S. Application Data

(60) Provisional application No. 61/512,097, filed on Jul. 27, 2011.

(51) Int. Cl.
*G01N 33/547* (2006.01)
*G01N 33/538* (2006.01)
*G01N 33/53* (2006.01)

(52) U.S. Cl.
USPC .............................. 436/532; 436/541; 435/7.1

(58) Field of Classification Search
None
See application file for complete search history.

(56) References Cited

U.S. PATENT DOCUMENTS

| | | | |
|---|---|---|---|
| 4,043,869 A | 8/1977 | Barker et al. | |
| 4,323,486 A | 4/1982 | Suzuki et al. | |
| 5,196,478 A | 3/1993 | Varga et al. | |
| 5,945,520 A | 8/1999 | Burton et al. | |
| 6,498,236 B1 | 12/2002 | Lihme et al. | |
| 6,908,556 B2 | 6/2005 | Sublette | |
| 7,018,538 B2 | 3/2006 | Leiser et al. | |
| 7,144,743 B2 | 12/2006 | Boschetti et al. | |
| 7,658,994 B2 | 2/2010 | Lakshmi | |
| 2001/0039043 A1 | 11/2001 | Lihme et al. | |
| 2007/0244307 A1 | 10/2007 | Engstrand et al. | |
| 2007/0299251 A1 | 12/2007 | Lihme | |
| 2010/0160605 A1 | 6/2010 | Komiya et al. | |
| 2011/0105736 A1 | 5/2011 | Masumoto et al. | |
| 2013/0253142 A1 | 9/2013 | Masumoto et al. | |

FOREIGN PATENT DOCUMENTS

| | | |
|---|---|---|
| DE | 289 204 A5 | 4/1991 |
| EP | 2 301 950 A1 | 3/2011 |
| EP | 2 551 013 A1 | 1/2013 |
| JP | 2010-029845 A | 2/2010 |
| KR | 2011-0037930 A | 4/2011 |
| WO | WO 2005/073711 A2 | 8/2005 |
| WO | WO 2005/08/2483 A1 | 9/2005 |
| WO | WO 2011/044637 A1 | 4/2011 |

OTHER PUBLICATIONS

Li et al. Reactive self-assembled monolayers on flat and nanoparticle surfaces, and their application in soft and scanning probe lithographic nanofabricaiton technologies. J. Mater. Chem. 2004, vol. 14, pp. 2954-2971.*

(Continued)

*Primary Examiner* — Shafiqul Haq
(74) *Attorney, Agent, or Firm* — Leydig, Voit & Mayer, Ltd.

(57) ABSTRACT

Substrates comprising a solid support, a ligand, and a linker comprising at least one C, O, N, or S atom covalently connecting the solid support to the ligand, are disclosed, along with methods of using and making the substrates, and devices including the substrates.

9 Claims, 3 Drawing Sheets

(56) References Cited

OTHER PUBLICATIONS

Search Report, Singapore Application No. 201205548-9, dated Feb. 25, 2013.
El-Sonbati AZ et al., Polymer complexes XIX Structural chemistry of poly(2-acrylamido-1,2-diaminobenzerie) complexes, *Kull Soc. Chim. Fr.*, 128 (1991), pp. 623-626.
Kanamori A. et al., "Preparation of High-Capacity Affinity Adsorbents Using Formyl Carriers and Their Use for Low- and High-Performance Liquid Affinity Chromatography of Trypsin-Family Proteases", *Journal of Chromatography*, 363 (1986) pp. 231-242.
Pennadam S.S. et al., Control of a Multisubunit DNA Motor by a Thermoresponsive Polymer Switch, *J. Am. Chem. Soc.*, 126, (2004), pp. 13208-13209.
Extended European Search Report, Application No. 12178286.6, dated Dec. 10, 2012.
Toomik, R. et al., Eesti NSV Teaduste Akadeemia Toimetised, Keemia (1988) 37 (3), pp. 195-200.
Notice of Reasons for Rejection, Japanese Application No. P2012-164890, dated Oct. 29, 2013.
Notice of Non-Final Rejection, Korean Application No. 10-2012-0062764, dated Oct. 30, 2013.
Tosoh Bioscience, 2010-11 Chromatographic Process Media Catalog, published Dec. 31, 2010.

* cited by examiner

MIXED MODE LIGANDS

CROSS-REFERENCE TO RELATED APPLICATIONS

This patent application claims the benefit of U.S. Provisional Patent Application No. 61/512,097, filed Jul. 27, 2011, which is incorporated by reference.

BACKGROUND OF THE INVENTION

The present invention relates generally to mixed-mode or multi-modal interaction chromatographic materials. The increasing need for bulk quantities of biologically relevant molecules (i.e., biomolecules) such as proteins has spawned a variety of techniques for isolating such biomolecules from physiological isolates. One separation methodology of particular interest is liquid chromatography.

There is a need in the art for mixed-mode chromatographic materials that exhibit high binding capacity, specificity, and recovery, and that can be regenerated extensively without degradation in chromatographic performance.

BRIEF SUMMARY OF THE INVENTION

In accordance with embodiments of substrates and methods of using substrates according to the invention, biological substances, such as immunoglobulins (preferably monoclonal antibodies), are preferably bound, while not binding aggregates. In some embodiments, the immunoglobulins IgA and/or IgM are selectively bound. Advantageously, biological substances can be purified while simultaneously removing aggregates, allowing for one-step purification and aggregate removal.

In an embodiment, the present invention provides a substrate comprising a solid support, a ligand, and a linker. In some embodiments, the linker comprises at least one C, O, N, or S atom covalently connecting the solid support to the ligand.

In an embodiment, the ligand has the formula

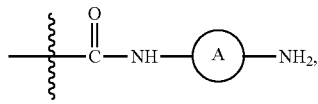

wherein

represents an aromatic or heteroaromatic group, which may be optionally substituted. In some embodiments, the aromatic or heteroaromatic group may be monocyclic or bicyclic, having 5-12 atoms in the ring system, and comprising 0-3 heteroatoms selected from O, N, and S.

In some embodiments, the ligand has a formula selected from the group consisting of

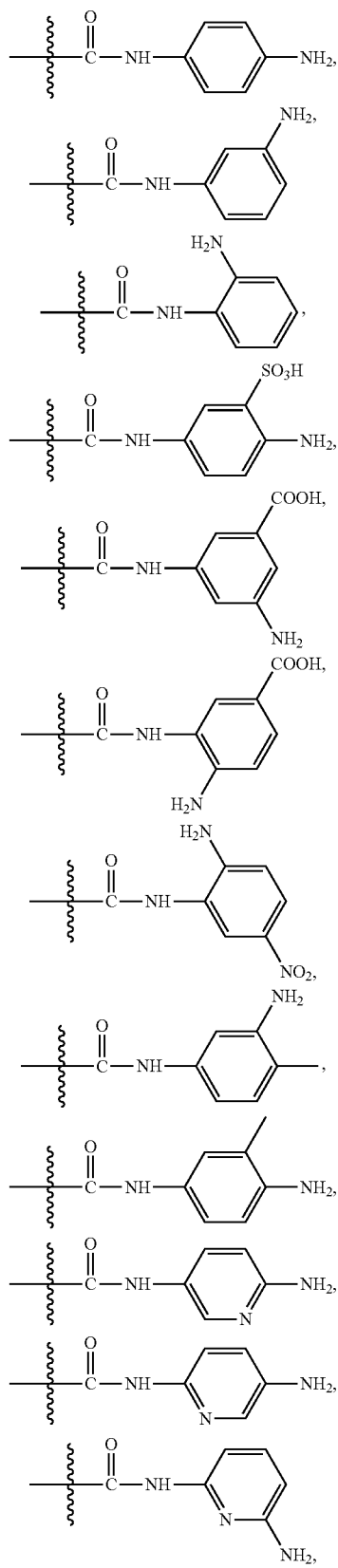

3
-continued
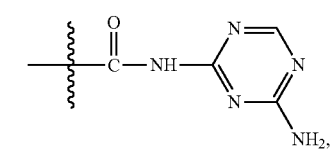
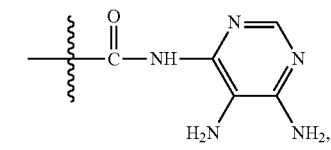
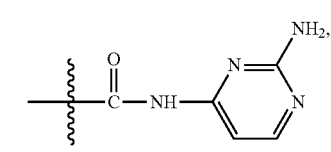
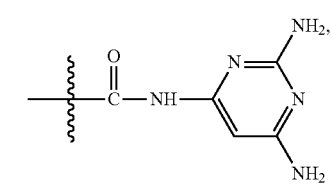
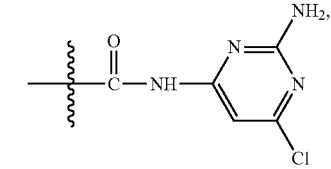
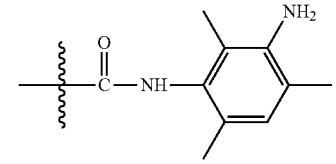
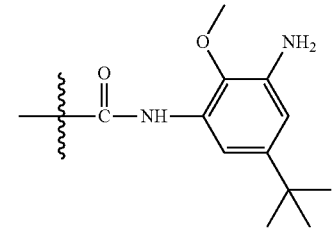
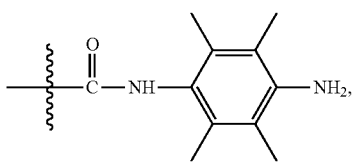
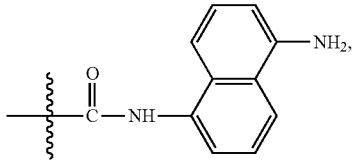
4
-continued
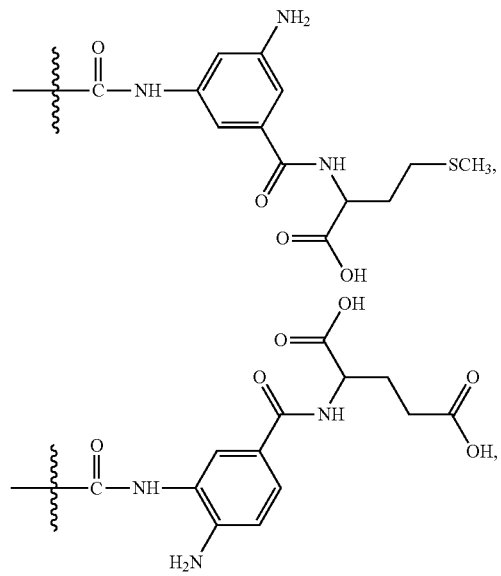
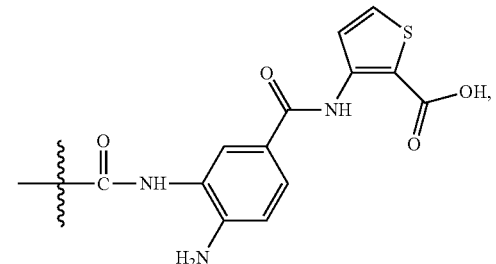
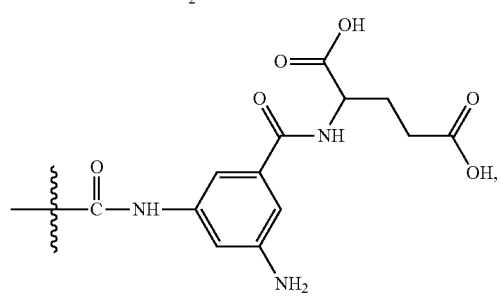
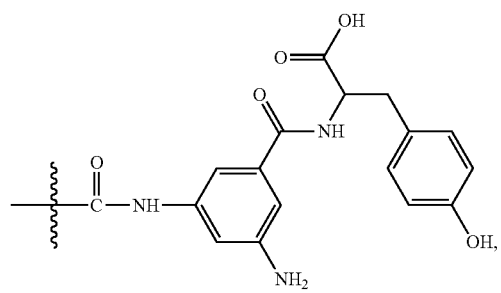
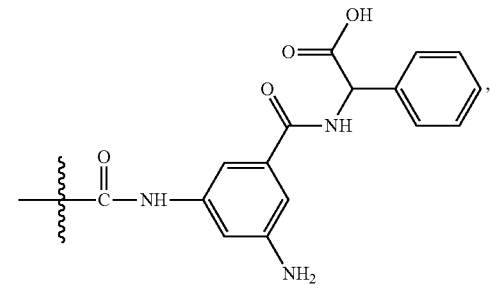

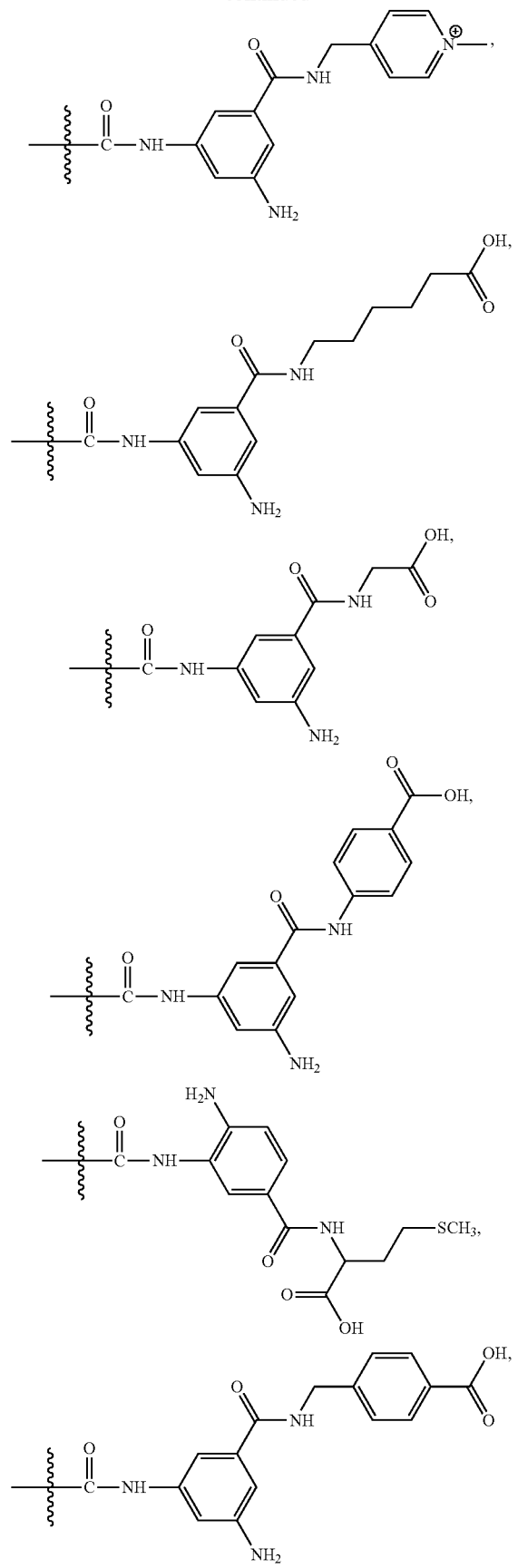
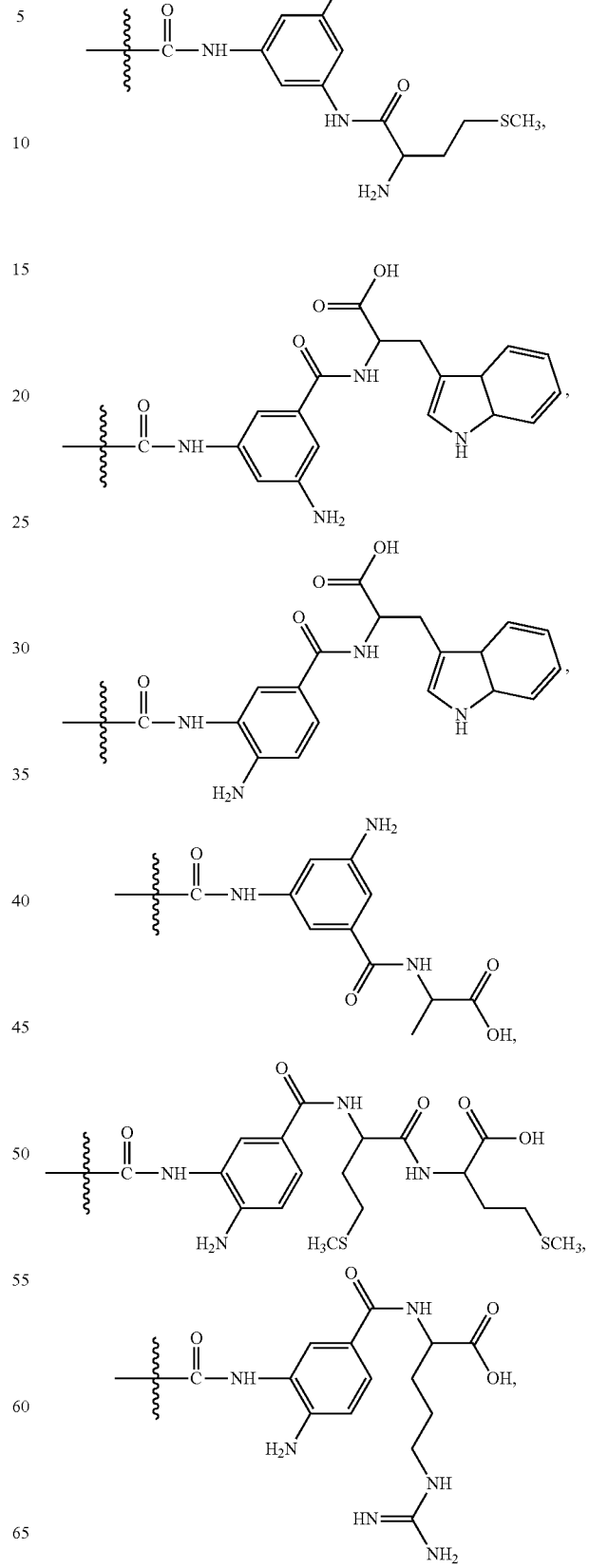

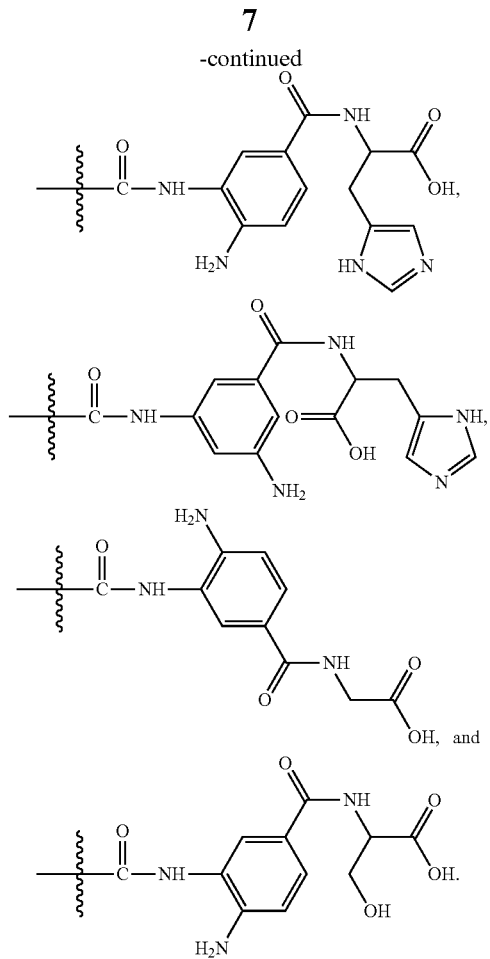

The wavy line in the above formulae indicates the position on the ligand at which the linker is connected.

In other embodiments, the ligand has the formula

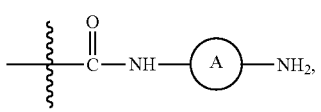

wherein

represents an aromatic or heteroaromatic ring selected from the group consisting of phenyl, pyridyl, pyrimidinyl, and naphthyl, optionally substituted with 0-4 substituents selected from the group consisting of —H, —($C_1$-$C_6$) alkyl, halogen, —OH, —O($C_1$-$C_6$) alkyl, —COOH, —COO($C_1$-$C_6$) alkyl, —$SO_3H$, —$PO_3H$, —$NO_2$, —$NH_2$,

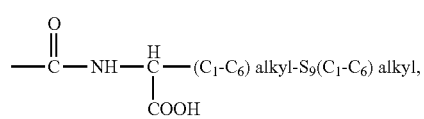

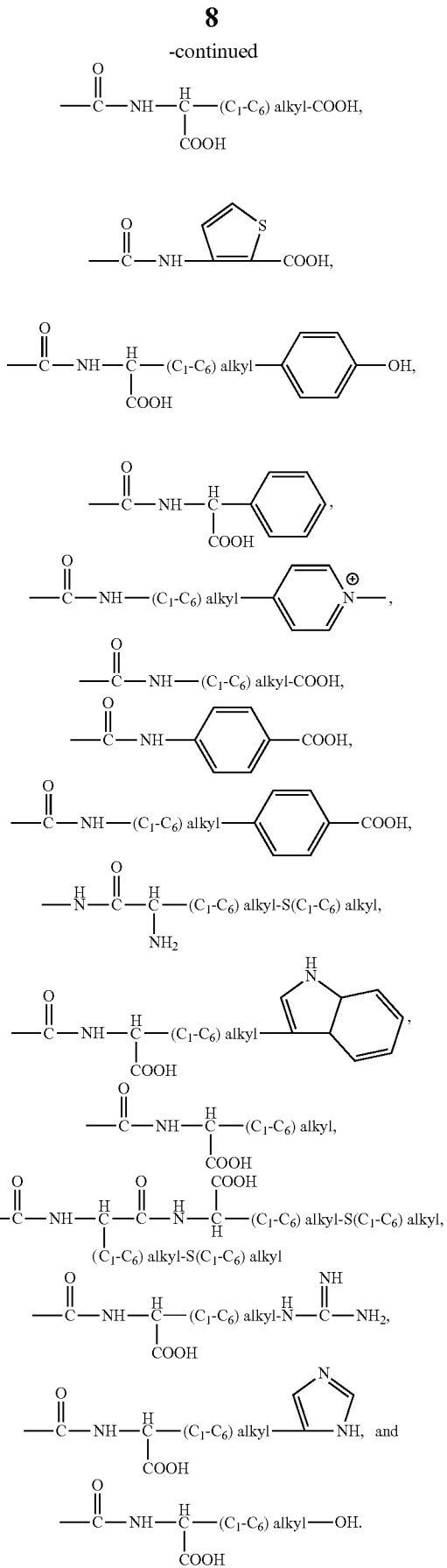

In some embodiments,

represents phenyl, pyridyl, or naphthyl, optionally substituted with 0-1 substituents selected from the group consisting of —H, —COOH, and —SO$_3$H. In other embodiments,

represents phenyl, optionally substituted with 0-1 substituents selected from the group consisting of —H, —COOH, and —SO$_3$H. In additional embodiments,

represents phenyl, optionally substituted with 0-1 substituents selected from the group consisting of

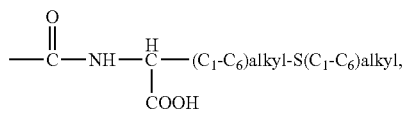

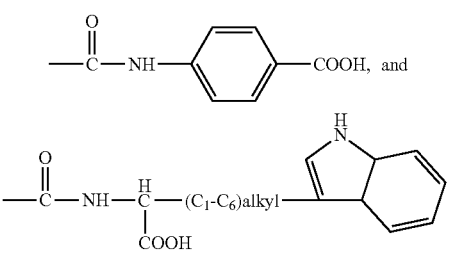

In yet other embodiments, the invention provides a substrate having a formula selected from the group:

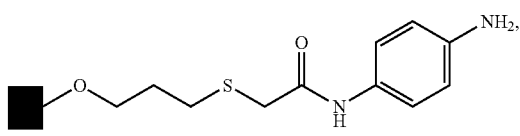

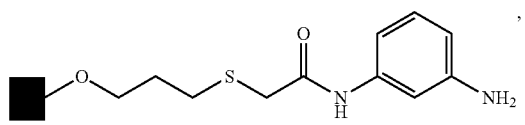

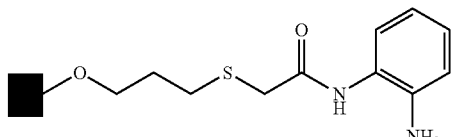

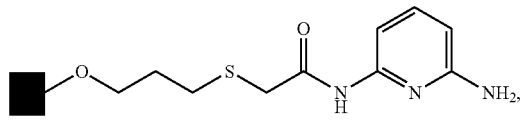

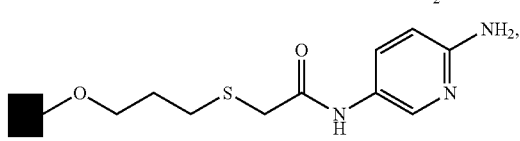

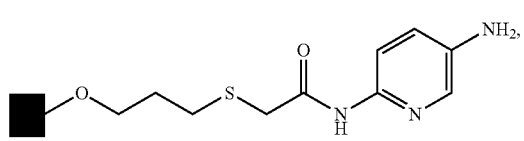

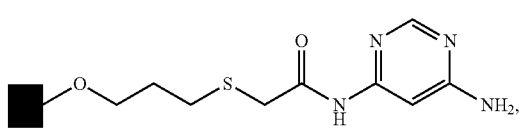

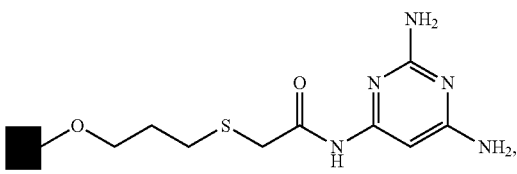

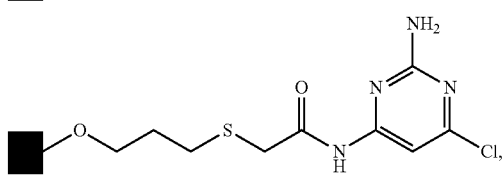

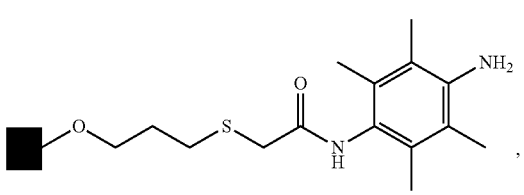

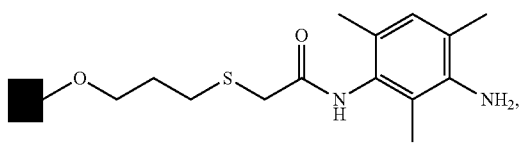

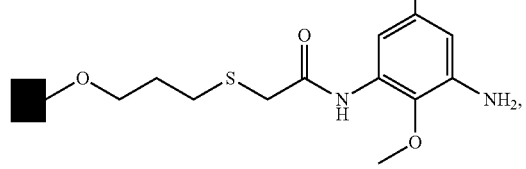

-continued
11
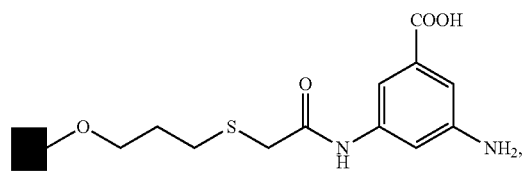
12
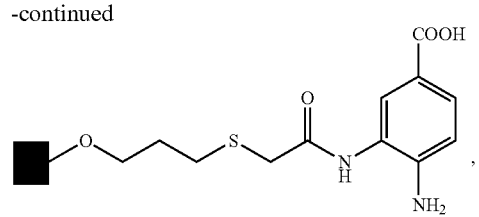
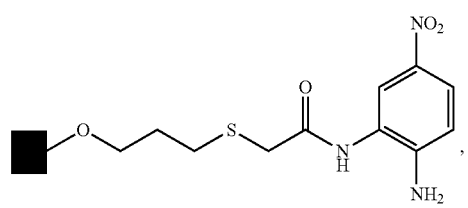
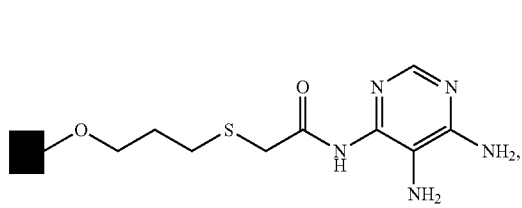
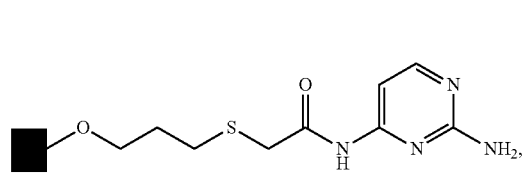
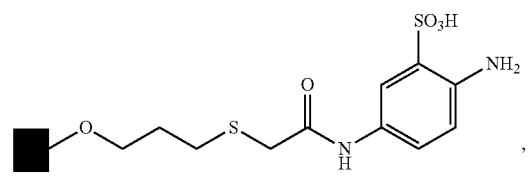
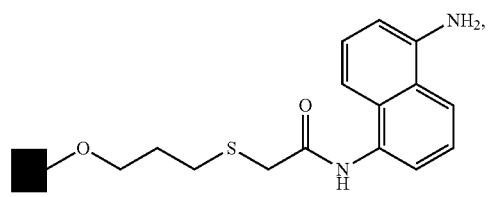
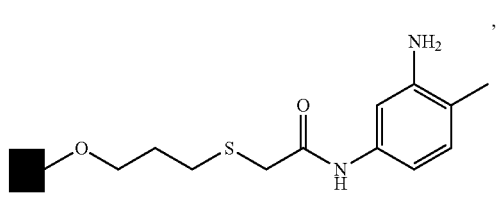
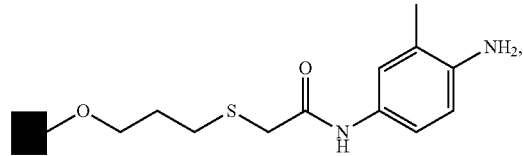
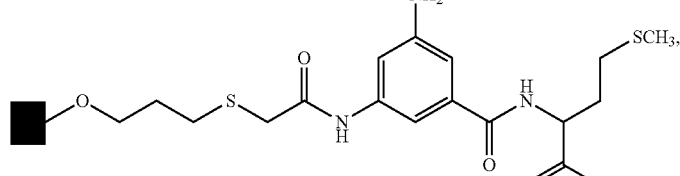
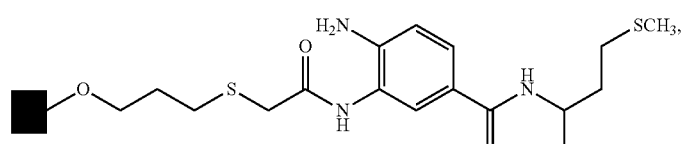
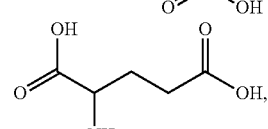
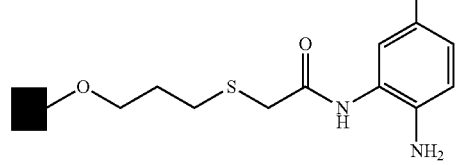

-continued
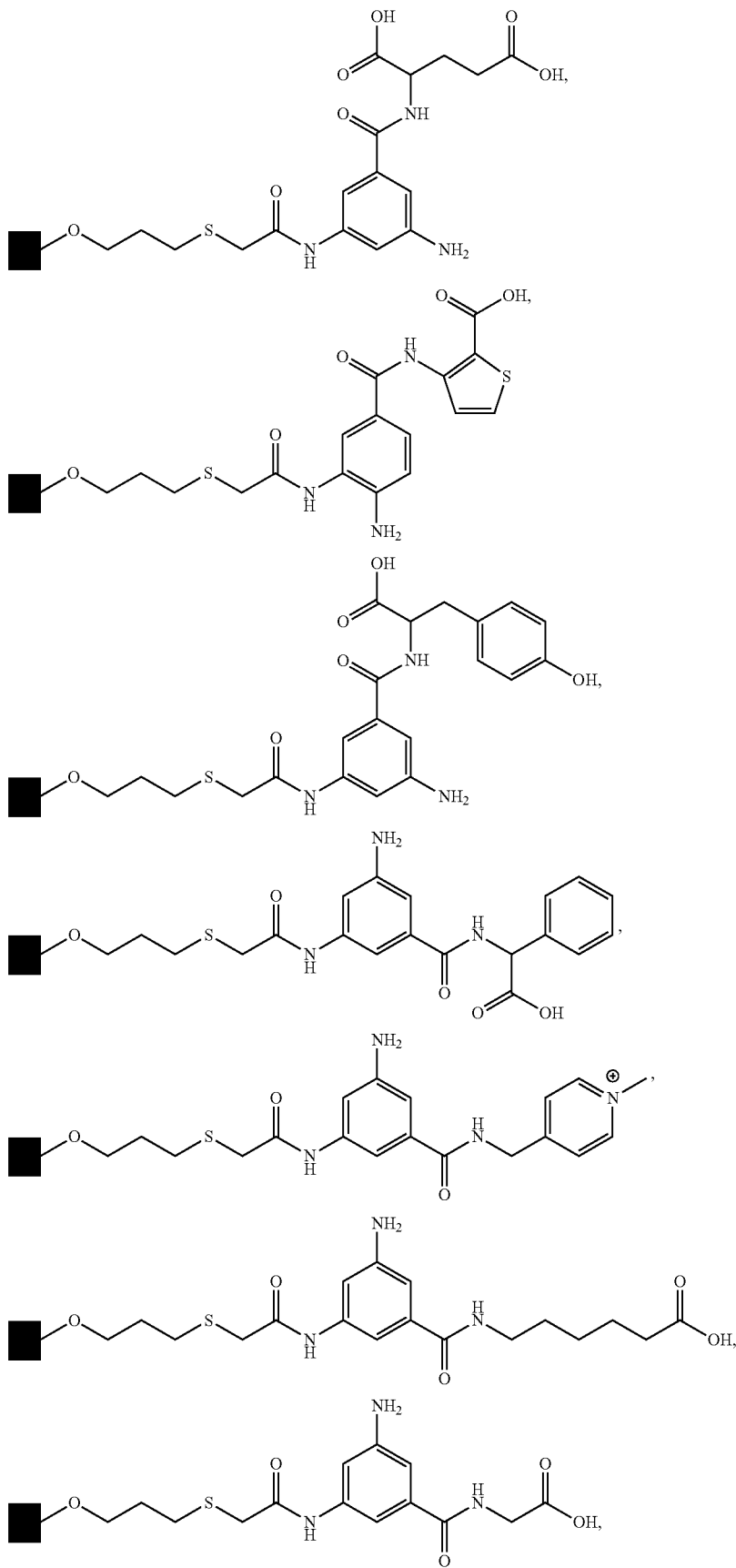

-continued
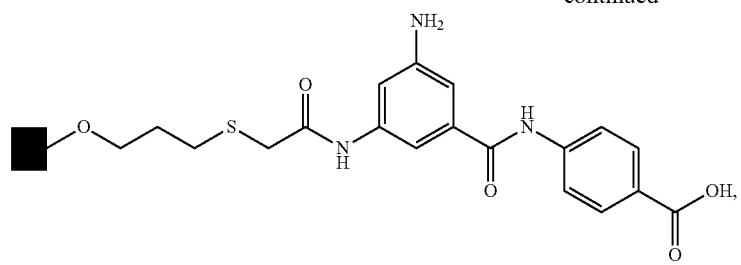
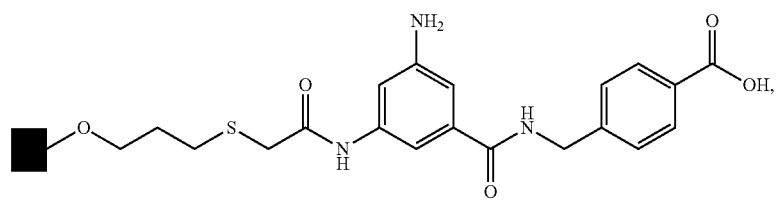
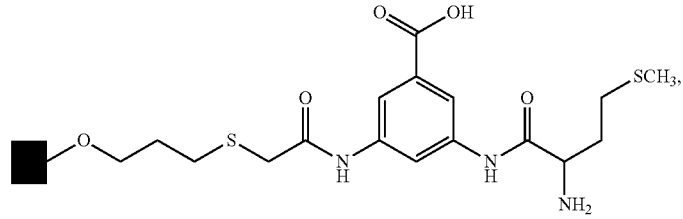
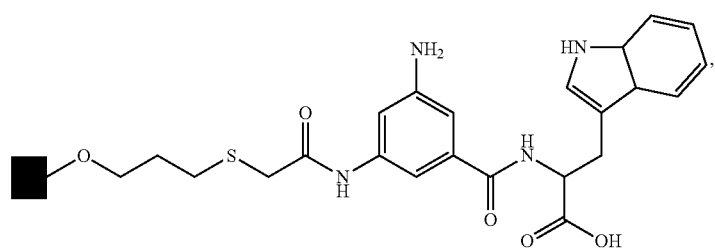
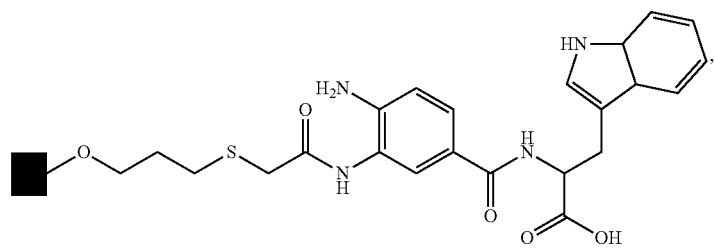
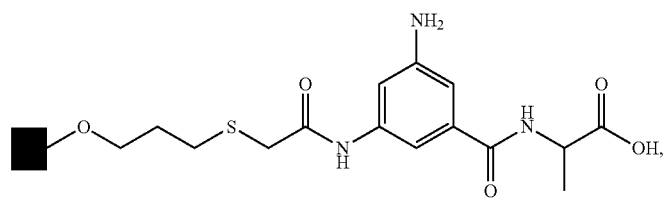
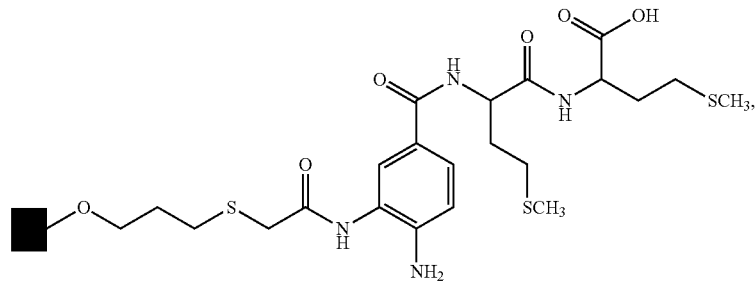

-continued

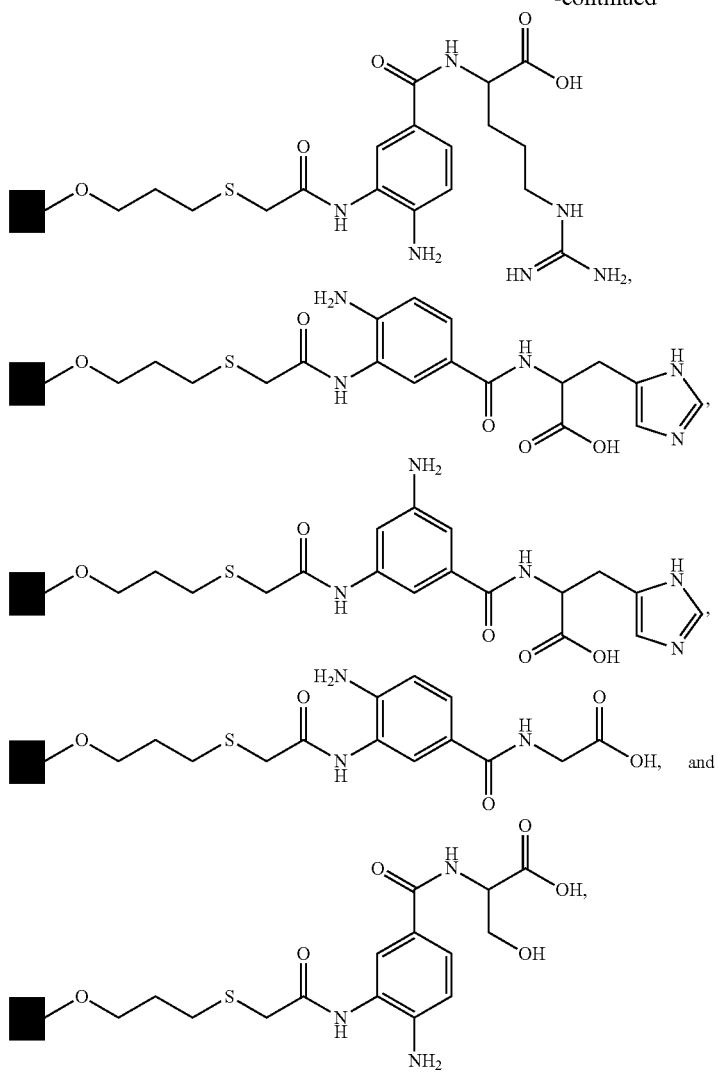

in which the black rectangle represents a solid support.

The invention also provides for the separation of at least one substance from a sample. In one embodiment, a method of treating a sample comprising at least one biological substance with a substrate comprises contacting the substrate with the sample for a period of time sufficient to allow the at least one biological substance in the sample to bind to the substrate. In a preferred embodiment, the method comprises (a) contacting a substrate according to an embodiment of the invention with a liquid sample that comprises at least one substance, wherein the substance adsorbs to the substrate; and (b) adjusting the pH, ionic strength, or both such that the substance desorbs from the substrate. In a typical embodiment, the method further comprises washing the substrate obtained in (a) with an equilibrium buffer.

In another embodiment, a process for making the substrate is provided, comprising activating the solid support by contacting the solid support with one functionality of a bifunctional reagent that comprises part or all of the linker to bind the reagent to the solid support. The activated solid support is subsequently reacted with a reagent that comprises the ligand to form a bond between the linker and the ligand.

BRIEF DESCRIPTION OF THE SEVERAL VIEWS OF THE DRAWING(S)

DETAILED DESCRIPTION OF THE INVENTION

Figure 1:
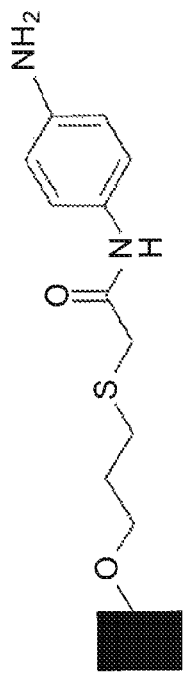
FIG. 1 is a graph showing the varied ligand density and dynamic binding capacity (DBC) using a substrate according to an embodiment of the invention.
Figure 1:
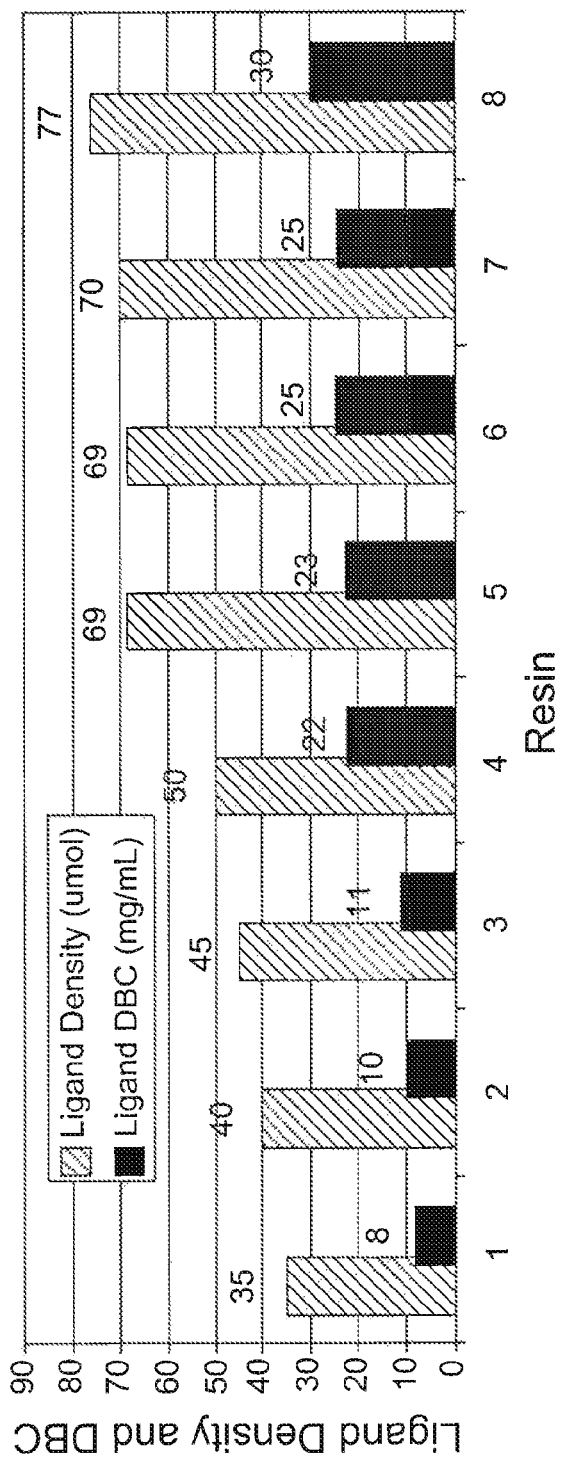

Embodiments of the present invention provide substrates that are effective adsorbents for use in separating and isolating a variety of substances, including biological substances of interest. Substrates according to embodiments of the invention may be used, for example, in preparative techniques, such as column chromatography.

One advantage of an embodiment of the substrate described herein is its high selectivity and specificity for biological substances such as proteins. Alternatively, or additionally, another advantage is the high biological molecule binding capacity of embodiments of the present substrates. Accordingly, it is possible to manipulate smaller volumes of a sample, to reduce processing time and/or to process a large amount of a sample per unit column volume. Another advantage of embodiments of the invention is the substrate's selectivity for proteins in the presence of protein aggregates. This can allow one-step purification and removal of aggregates from protein samples. Additionally, substrates can be prepared cost-effectively.

The substrate comprises a solid support and a ligand that is covalently attached to the solid support via a linker. In some embodiments, the linker comprises at least one C, O, N, or S atom.

In an embodiment, the ligand has the formula

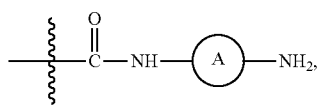

wherein

represents an aromatic or heteroaromatic group, which may be optionally substituted. In some embodiments, the aromatic or heteroaromatic group may be monocyclic or bicyclic, having 5-12 atoms in the ring system, and comprising 0-3 heteroatoms selected from O, N, and S.

In some embodiments, the ligand has a formula selected from the group consisting of

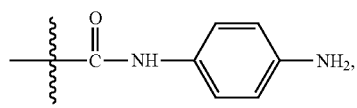

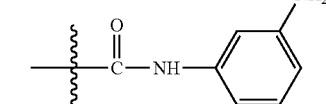

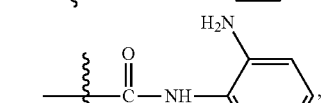

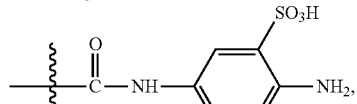

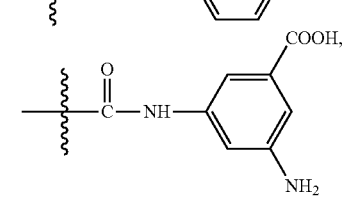

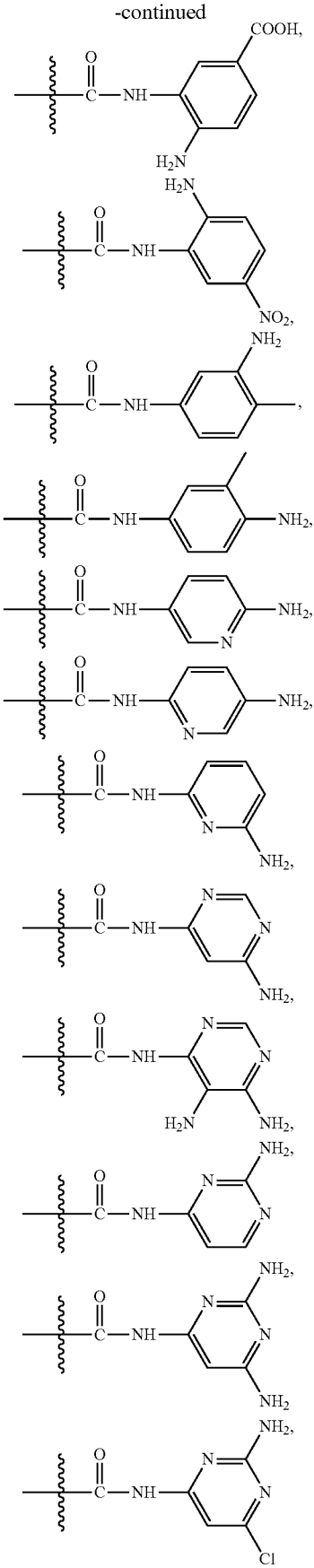

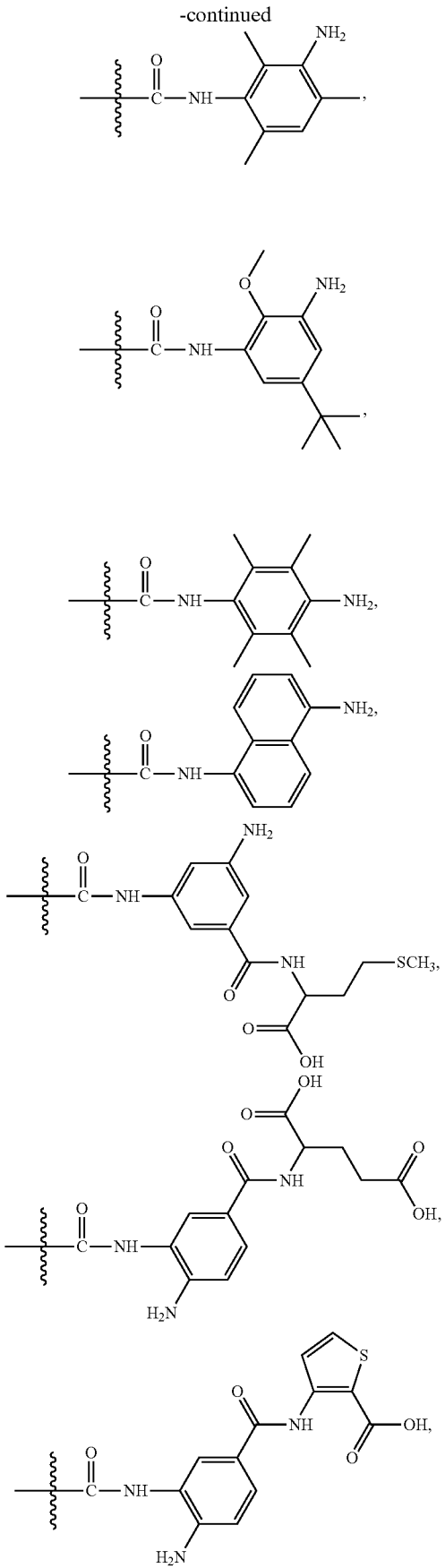
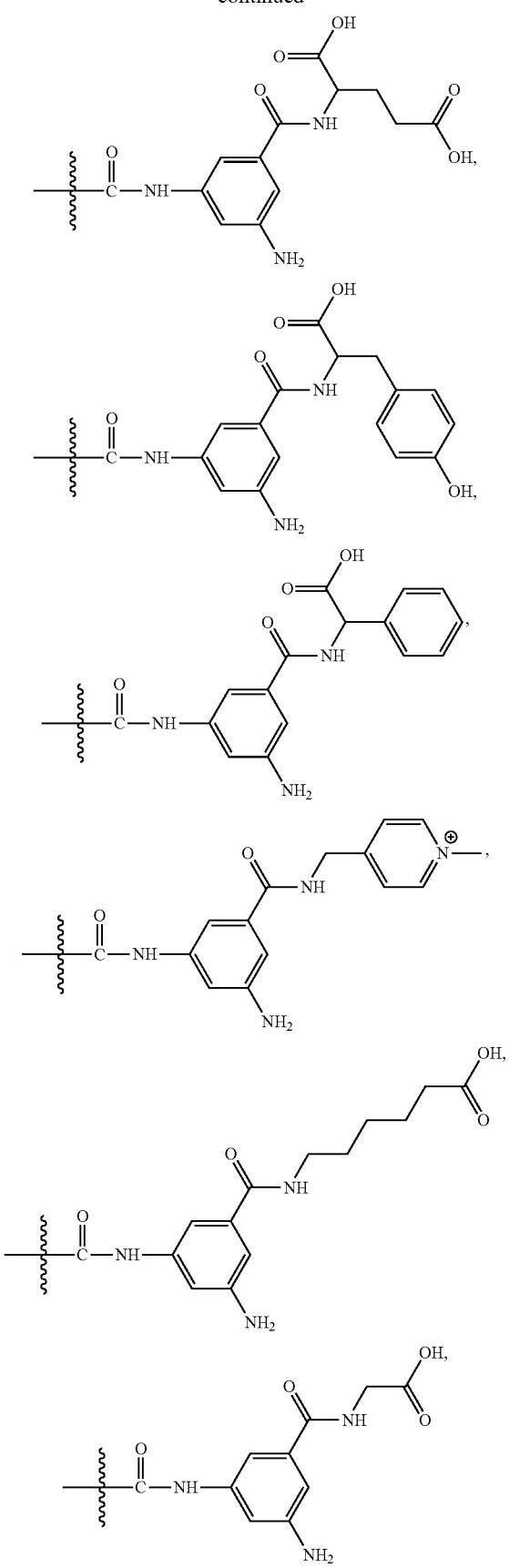

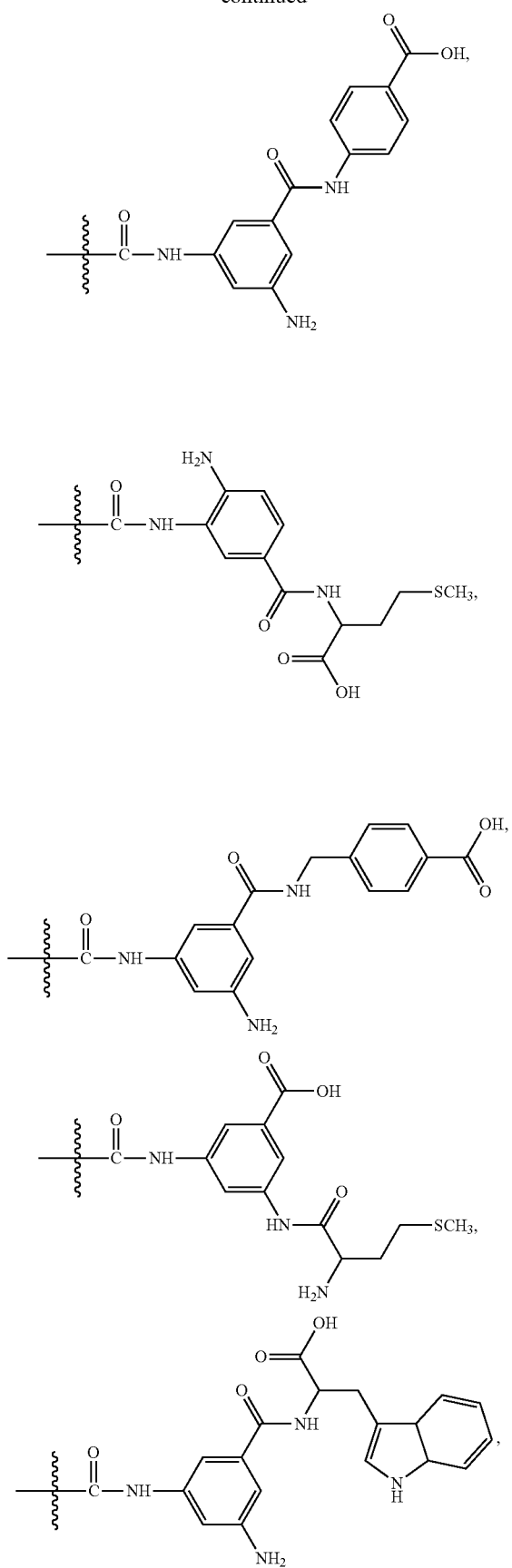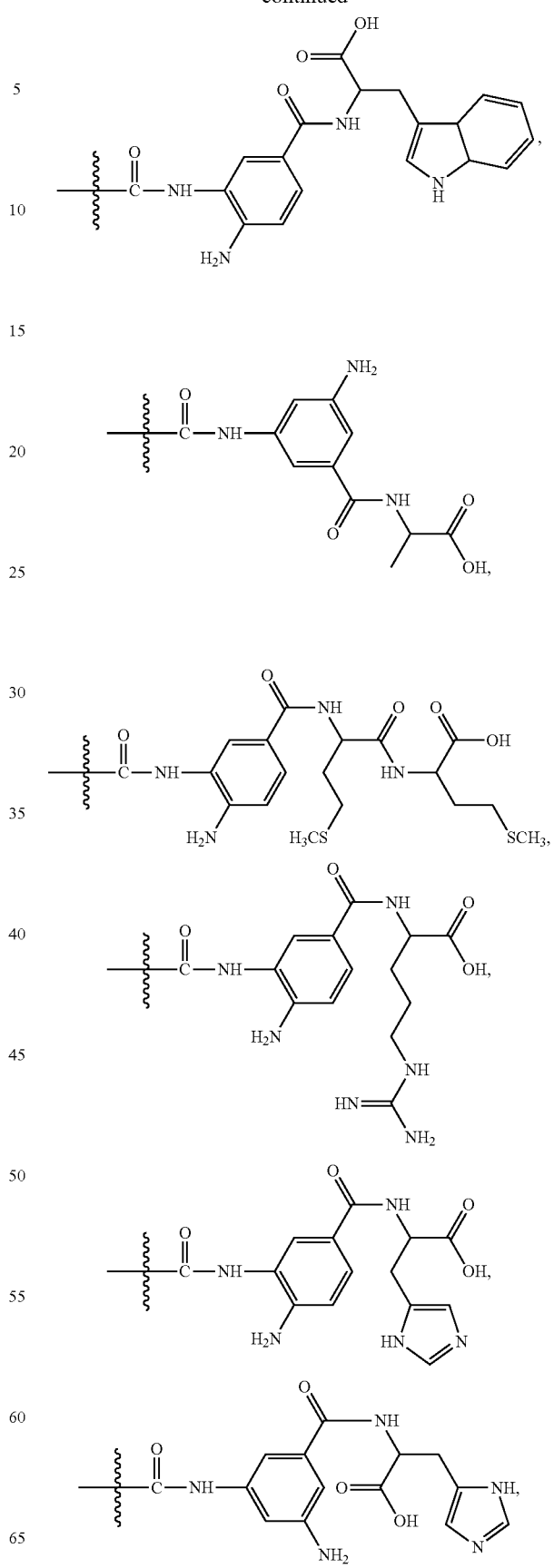

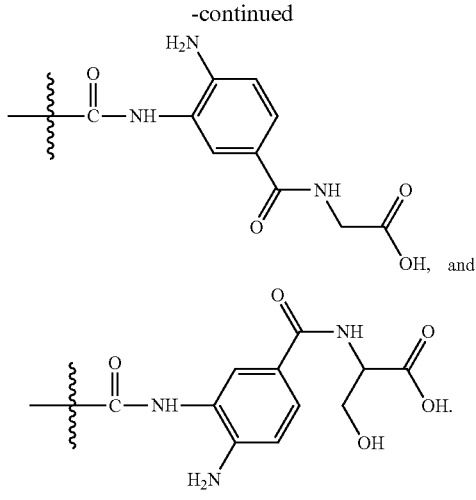

The wavy line in the above formulae indicates the position on the ligand at which the linker is connected.

In other embodiments, the ligand has the formula

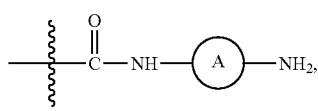

wherein

represents an aromatic or heteroaromatic ring selected from the group consisting of phenyl, pyridyl, pyrimidinyl, and naphthyl, optionally substituted with 0-4 substituents selected from the group consisting of —H, —($C_1$-$C_6$) alkyl, halogen, —OH, —O($C_1$-$C_6$) alkyl, —COOH, —COO($C_1$-$C_6$) alkyl, —$SO_3H$, —$PO_3H$, —$NO_2$, —$NH_2$,

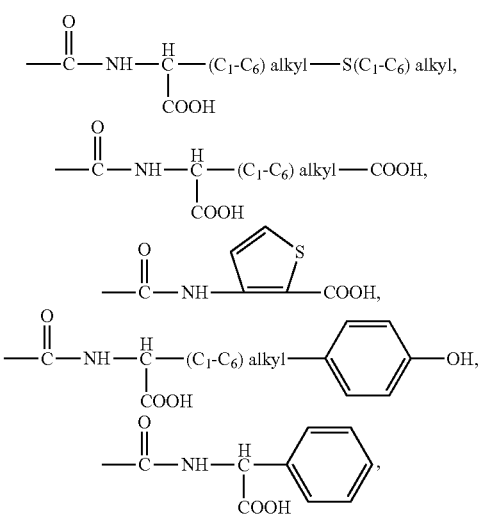

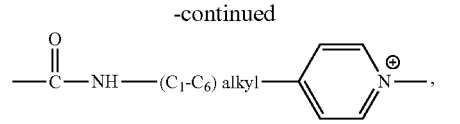

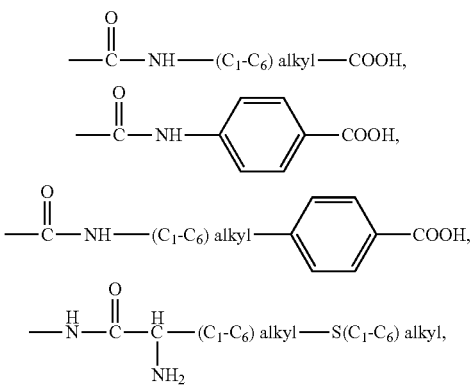

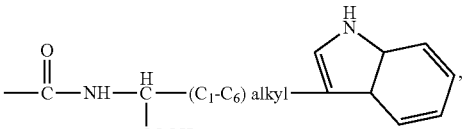

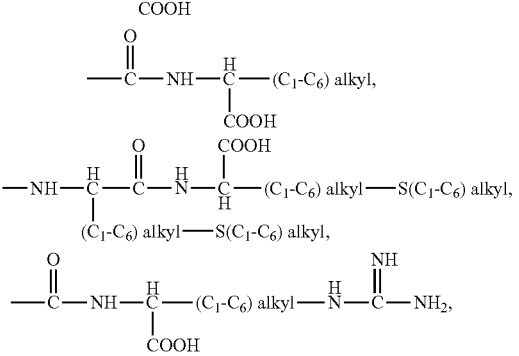

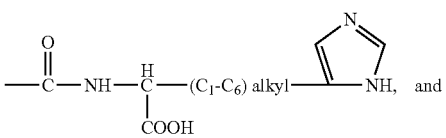

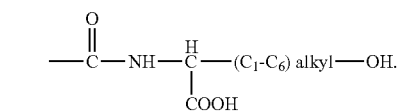

In some embodiments,

represents phenyl, pyridyl, or naphthyl, optionally substituted with 0-1 substituents selected from the group consisting of —H, —COOH, and —$SO_3H$. In other embodiments,

represents phenyl, optionally substituted with 0-1 substituents selected from the group consisting of —H, —COOH, and —SO₃H. In additional embodiments,

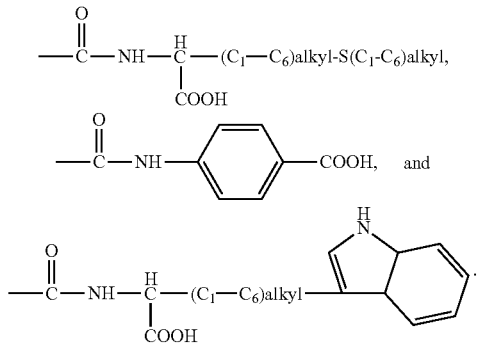

represents phenyl, optionally substituted with 0-1 substituents selected from the group consisting of

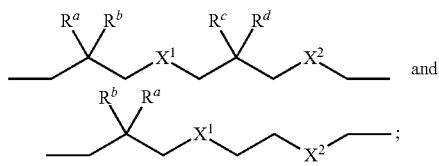

The ligand is covalently connected to the linker, which links the ligand to the solid support. The linker may reduce steric hindrance and increase the accessibility of the ligand to the substance to be bound. The connection between the ligand and the linker may be, for example, an amide bond.

The linker typically comprises at least one C, O, N, or S atom. In an embodiment, the linker comprises —(CH$_2$)$_m$X(CH$_2$)$_n$— or —(CH$_2$)$_m$X$^1$(CH$_2$)$_n$X$^2$(CH$_2$)$_p$—, wherein X, X$^1$, and X$^2$ are each independently selected from O, S, NH, and a covalent bond; and m, n, and p are each independently 0, 1, 2, 3, 4, 5, or 6. In another embodiment, 1, 2, or 3 of the H atoms in the above formulae may be replaced with an equivalent number of OH groups and/or methyl groups.

In an embodiment, the linker comprises a structure selected from the group:

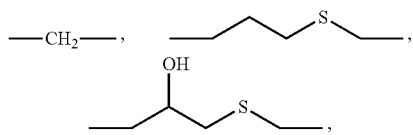

in which each of X$^1$ and X$^2$ is independently selected from O, S, and NH; and each of R$^a$, R$^b$, R$^c$, and R$^d$ is independently selected from H, OH, and methyl.

In another embodiment, the linker comprises a structure selected from the group:

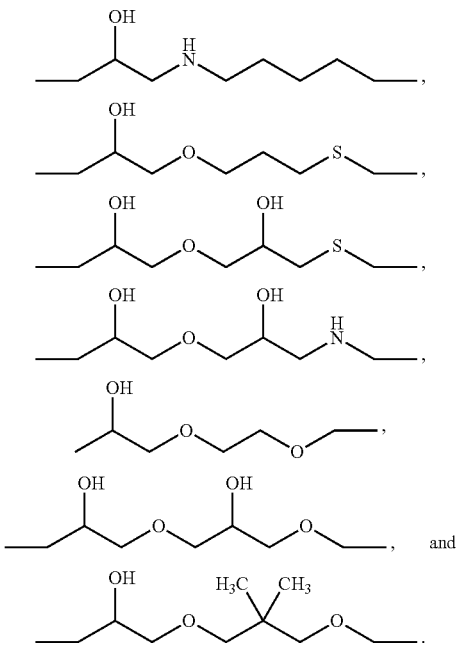

The linker connects the ligand to a solid support. The solid support may be of the form typically used for chromatography media, e.g., porous or non-porous beads or irregular particles, of, for example, about 0.1 μm to about 1000 μm in diameter. These beads or particles can be derivatized with the combination linker and ligand. The beads or particles can provide a chromatography medium that one can use to pack a column, for example. Alternatively, in some embodiments, the solid support comprises fibers, membranes, or sponge-like materials permeated with openings or pores in, for example, the micron to multi-millimeter sizes.

Suitable solid supports are known in the art. In an embodiment, the solid support may comprise an organic material. Exemplary organic materials are polysaccharides, such as cellulose, starch, agar, agarose, and dextran. Synthetic polymers are contemplated, including substituted or unsubstituted polyacrylamides, polymethacrylamides, polyacrylates, polymethacrylates, polyvinyl polymers such as polyvinyl alcohol, polystyrene, polysulfone, and copolymers of styrene and divinylbenzene, and mixtures thereof. In another embodiment, inorganic materials may be used as the solid support material. Such inorganic materials include but are not limited to porous mineral materials, such as silica; hydrogel-containing silica, zirconia, titania, alumina; and other ceramic materials. It is also possible to use mixtures of these materials, or composite materials formed by copolymerization of or by an interpenetrated network of two materials, such as those disclosed in U.S. Pat. Nos. 5,268,097; 5,234,991; and 5,075,371.

In an embodiment, the inventive substrate exhibits ligand densities (number of ligands per volume of substrate) of at least about 20 μmol/ml substrate, at least about 30 μmol/ml, or at least about 40 μmol/ml, or at least about 50 μmol/ml. In some embodiments, the ligand density is less than about 180 μmol/ml, for example, less than about 150 μmol/ml, or less than about 100 μmol/ml, or less than about 80 μmol/ml, or less than about 60 μmol/ml, or less than about 50 μmol/ml. The ligand density may be in the range of from about 20 μmol/ml to about 180 µmol/ml, from about 30 µmol/ml to about 150 µmol/ml, or from about 40 µmol/ml to about 100 µmol/ml, or from about 50 µmol/ml to about 80 µmol/ml, or from about 30 µmol/ml to about 60 µmol/ml, or from about 50 µmol/ml to about 60 µmol/ml.

Other embodiments of the invention are shown below. Here and throughout, a black rectangle in a formula represents a solid support.

In yet other embodiments, the invention provides a substrate having a formula selected from the group:

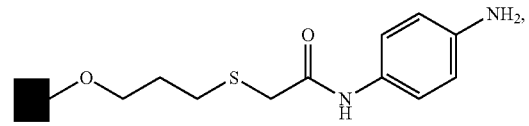

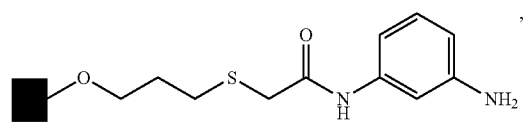

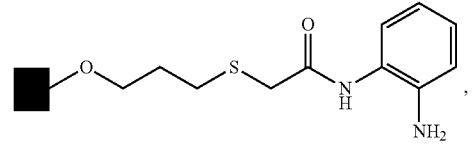

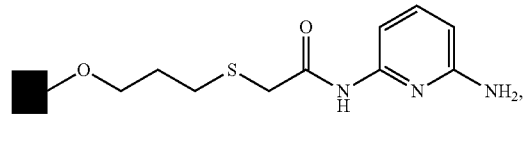

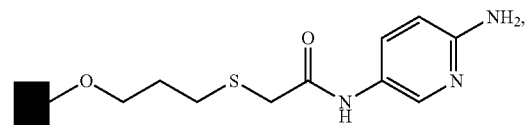

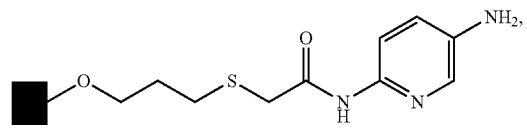

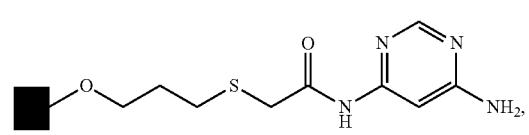

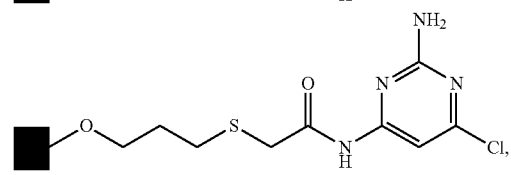

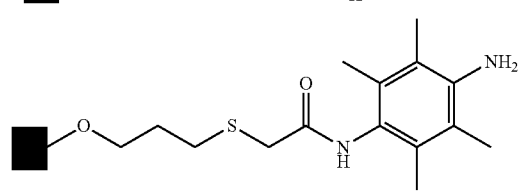

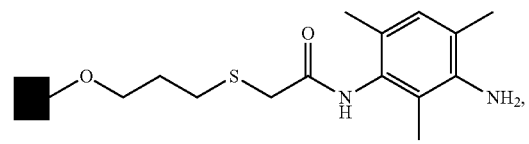

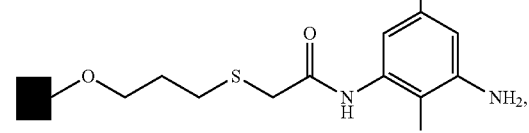

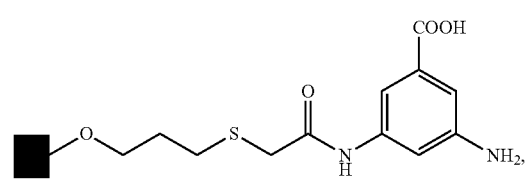

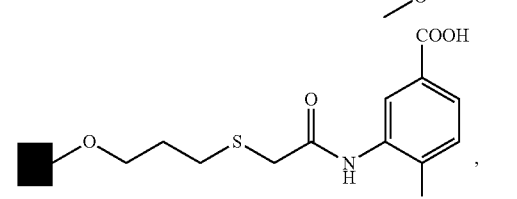

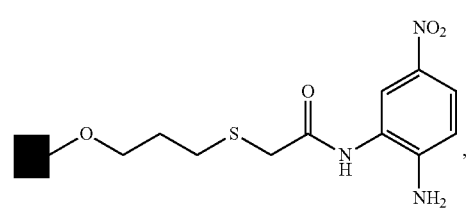

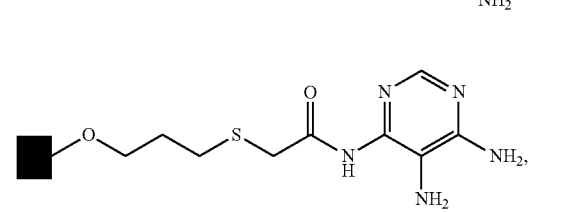

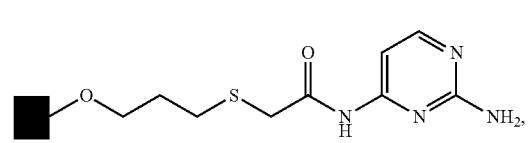

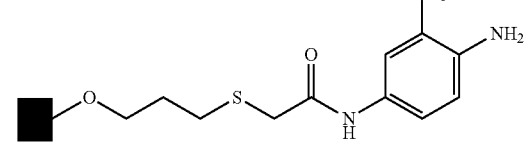

31 32
-continued
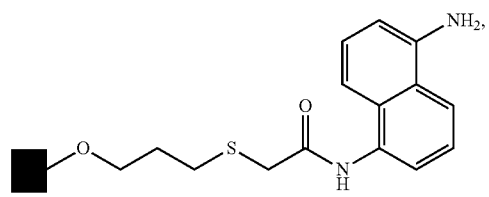
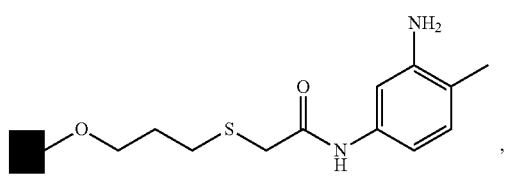
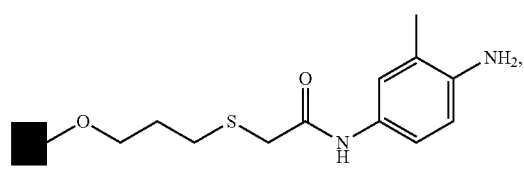
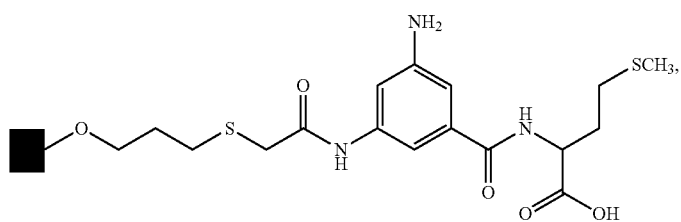
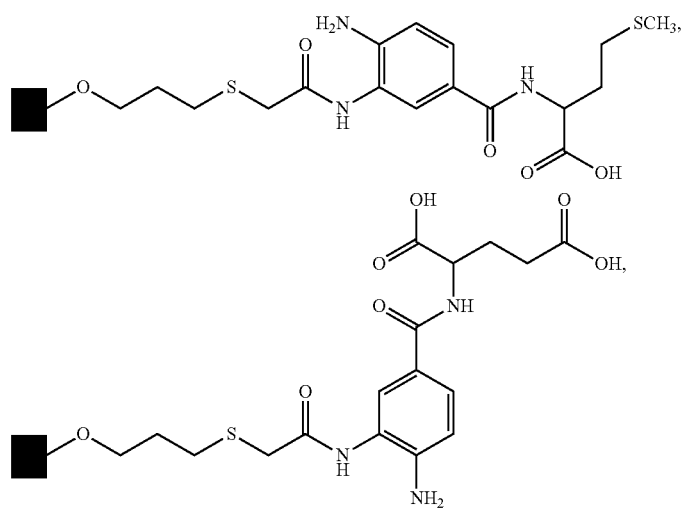
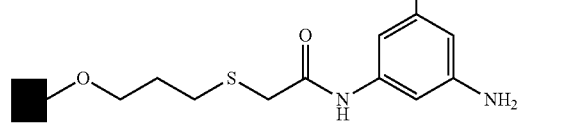
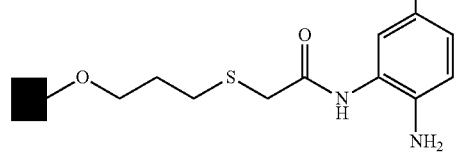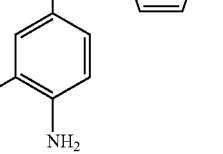

-continued
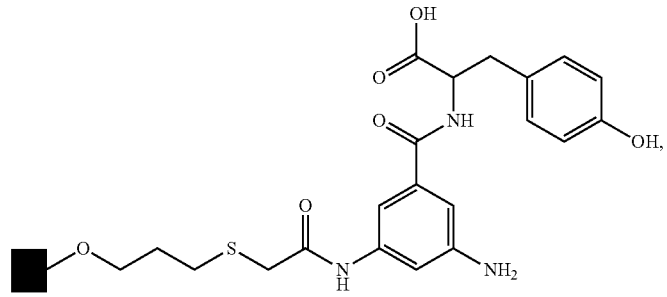
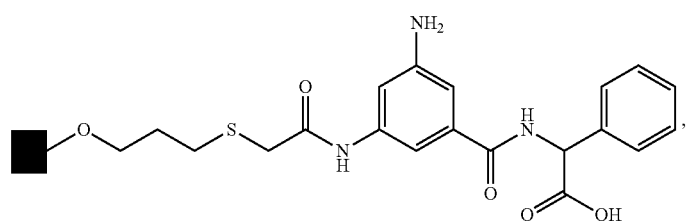
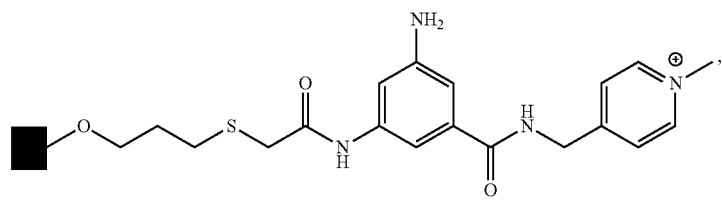
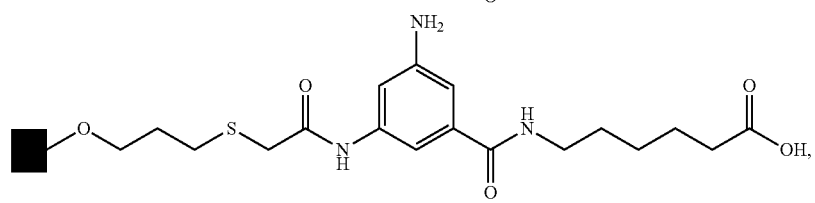
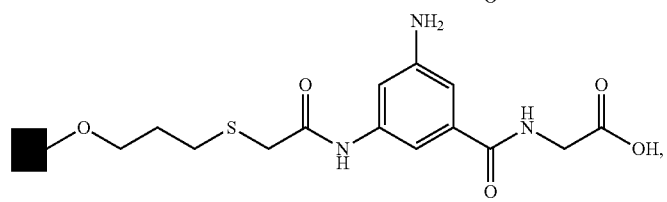
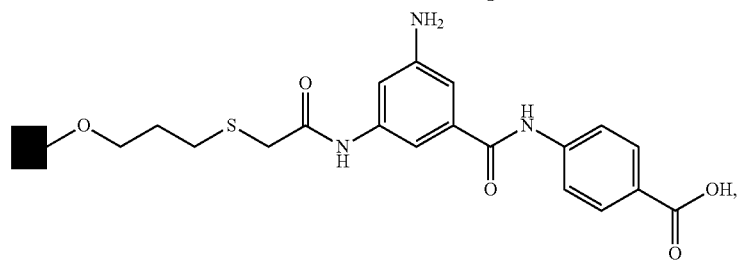
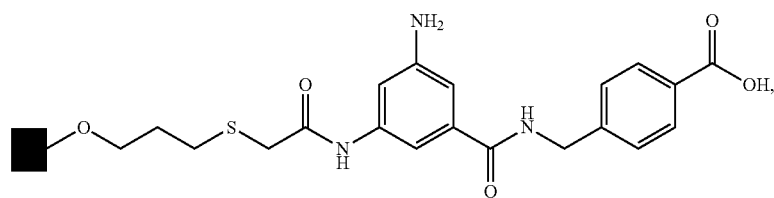

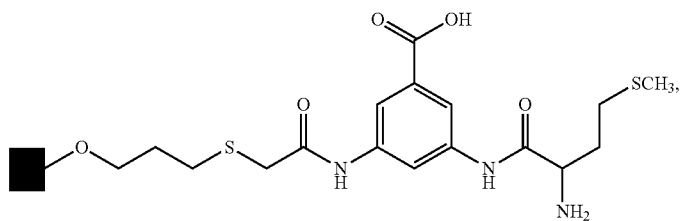
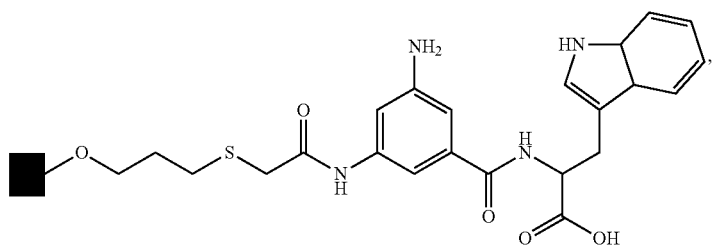
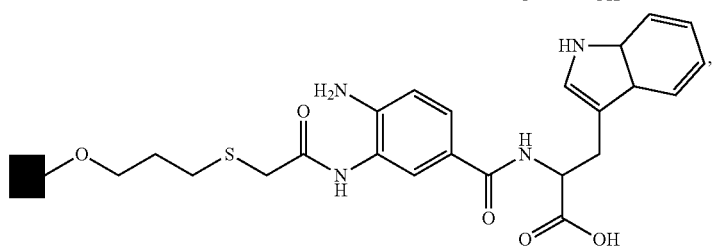
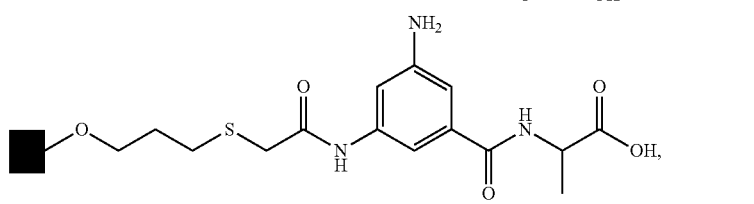
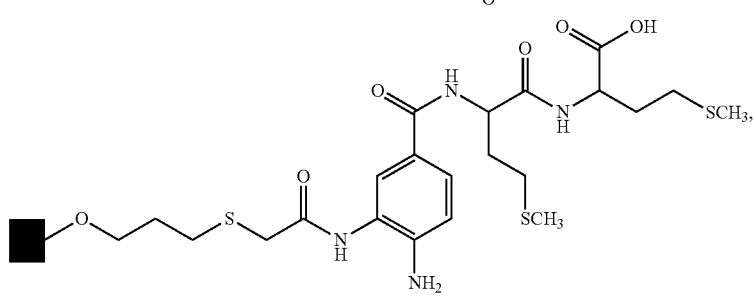
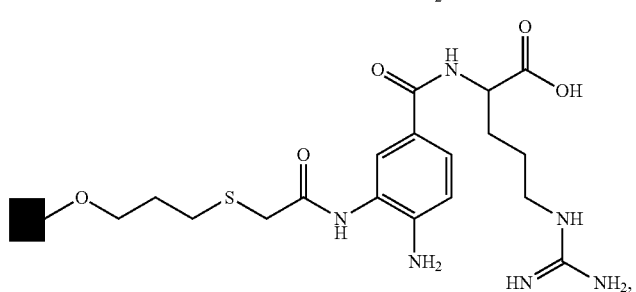
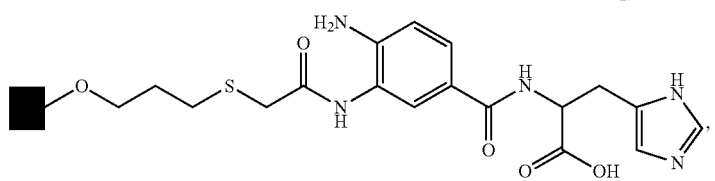

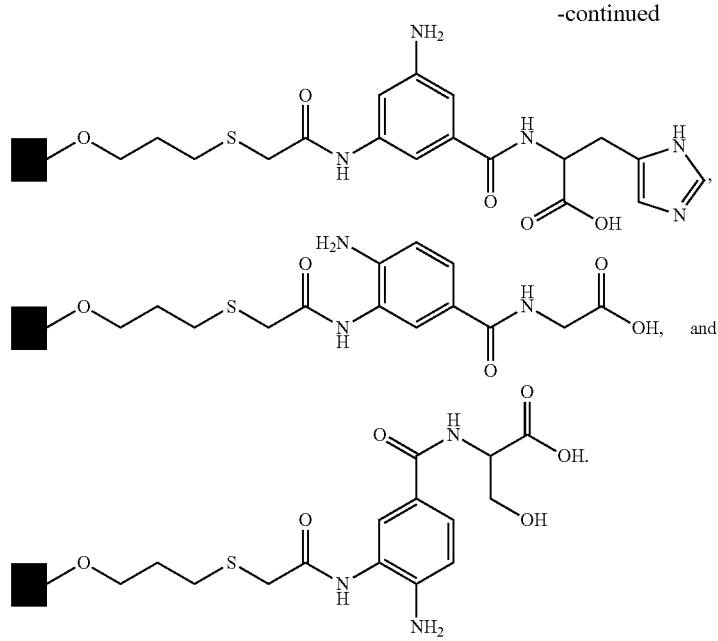

In another embodiment, the present invention comprises a chromatography column, comprising a tubular member having an inlet end and an outlet end and packed with an embodiment of the substrate described herein. The tubular member can be made of any suitable material, such as glass, plastic, or metal. The packed substrate can be abutted on one end, or on each end, by porous members disposed within the tubular member, which keep the substrate fixed within the tubular member.

In some embodiments, gravity flow of a liquid through a column is sufficient, e.g., for contacting a substrate with a liquid sample, washing fluid, and/or eluant. In other embodiments, the column may comprise one or more fluid moving devices to achieve an upward or downward flow of fluid through the column. Such devices include pumps, injectors, and any other device typically employed in association with chromatography equipment, as is known in the art.

The chromatography column can be of any suitable volume. For example, separations on a laboratory scale may warrant a column volume as small as, for example, about 1 milliliter or even about 1 microliter. Large scale purification and isolation of biological substances can be performed on columns as large as, for example, about 5000 liters. More typical volumes are, for example, between 1 liter and 100 liters. The column is tubular in general shape, but is not otherwise particularly limited in length or diameter. Depending upon the context in which the column is employed, the column diameter can vary between, for example, about 0.5 mm to about 1000 mm. Additionally, the column length can vary between, for example, about 50 mm to about 1000 mm. Thus, the invention contemplates columns of a variety of dimensions and corresponding volumes.

In an additional embodiment, the invention includes a process for making the substrate. The method generally comprises activating the solid support by contacting the solid support with one functionality of a bifunctional reagent that comprises part or all of the linker to bind the reagent to the solid support. The activated solid support is subsequently reacted with a reagent that comprises the ligand to form a bond between the linker and the ligand. The bifunctional reagent may comprise at least two functional groups including but not limited to chloro, bromo, iodo, epoxide, carboxyl, ester, aldehyde, ketone, amido, alkenyl, cyano, and imino.

Another embodiment of the invention is a method for the separation of at least one substance from a sample. In one embodiment, a method of treating a sample comprising at least one biological substance with a substrate comprises contacting a substrate according to an embodiment of the invention with the sample for a period of time sufficient to allow the at least one biological substance in the sample to bind to the substrate. In a preferred embodiment, the method comprises (a) contacting the substrate with a liquid sample that comprises at least one substance, wherein the substance adsorbs to the substrate; and (b) adjusting the pH, ionic strength, or both such that the substance desorbs from the substrate. In a typical embodiment, the method further comprises washing the substrate obtained in (a) with an equilibrium buffer.

Another embodiment of the invention includes a process for preparing the substrate. The ligand described above is chemically immobilized on the solid support by forming covalent bonds between the solid support and the linker, and between the linker and the ligand. Typically, the solid support is first treated with a bifunctional reagent that serves to introduce onto the solid support reactive groups that form part or all of the linker. For some solid supports, such as cellulose, composites containing a hydrogel, or other materials presenting hydroxyl groups, it may be advantageous to deprotonate the hydroxyl groups with a hydroxide source, for example, prior to reaction with a bifunctional reagent. The bifunctional reagent is capable of reacting both with the solid support and with reagents that contain the ligand. Illustrative bifunctional reagents, which contain the same or different functional groups, include but are not limited to epichlorohydrin, epibromohydrin, dibromo- and dichloropropanol, dibromobutane, ethylene glycol diglycidylether, butanediol diglycidylether, divinyl sulfone, allylglycidylether, and allyl bromide. Allyl heterofunctional compounds, such as allyl bromide, are preferred bifunctional reagents.

Once functionalized, the solid support is typically subsequently washed extensively with one or more solvents to remove unreacted bifunctional reagent, reaction byproducts, or both. A typical solvent used in this regard is water.

The ligands may be introduced by way of reagents that react with the functional groups presented by the functionalized solid support as described above. The ligand reagents may be prepared by synthetic processes known to those of skill in the art.

The particular pairing of a bifunctional reagent with a ligand reagent is guided by well-known chemistries. For example, solid supports that are functionalized with epoxides may undergo reactions with mercapto, hydroxy, or amino-containing reagents to furnish a substrate with ethylene-containing linking groups. Other solid supports that are modified with allyl bromide, for example, present alkene groups that can be reacted directly with mercapto-containing reagents, thereby providing linkers that contain sulfur atoms. Alternatively, the alkene groups can be further brominated to furnish suitably reactive bromo derivatives. In another illustrative method, a solid support may be allowed to react with a sulfur-containing bifunctional reagent such as divinylsulfone (DVS). In this instance, the reagent comprising the ligand need only to react with the vinyl group presented by the DVS-activated solid support.

In an alternative route, a solid support, activated as described above, may be treated with an intermediate bifunctional reagent. The product of this reaction may subsequently be treated with a reagent comprising the ligand. An illustrative example in this regard is the reaction between an allyl-activated solid support, as described above, with mercaptohexanoic acid. The resultant pendant carboxyl groups can be reacted with any convenient ligand reagent that bears, for example, a primary amine. In embodiments that employ this methodology, it may be necessary to use coupling reagents such as N-ethoxycarbonyl-2-ethoxy-1,2-dihydroquinoline (EEDQ) or commonly-known carbodiimides such as dicyclohexylcarbodiimide (DCC), 1-ethyl-3-(3-dimethylaminopropyl) carbodiimide (EDC), N,N'-diisopropylcarbodiimide (DIC), or 4-(4,6-dimethoxy-1,3,5-triazin-2-yl)-4-methylmorpholinium (DM-TMM).

The concentration of immobilized linker and ligand can vary as is known in the art between, for example, a fraction of a micromole to several hundred micromoles per milliliter of solid support, depending upon the concentration of bifunctional reagent used to make the solid support. Low concentrations of the immobilized group typically result in low separation capacity of the chromatographic material, whereas high concentrations generally lead to increased capacity.

In certain embodiments, the substrate of the present invention can be used to separate and, if desired, purify, a variety of substances, including biologically relevant molecules and biological substances such as antibodies, proteins, glycoproteins, fusion proteins, recombinant proteins, tagged proteins, enzymes and biological catalysts, peptides, cells, bacteria, viruses, virus-like particles (VLPs), vaccines, nucleic acids, carbohydrates, and lipids. Other substances that are suitable for separation (and, if desired, purification) include oligo- and polysaccharides, lipopolysaccharides, polypeptides, and synthetic soluble polymers. The biological substances typically derive from, or are contained in, sources including but not limited to liquid samples such as saliva, biological fluid, urine, lymphatic fluid, prostatic fluid, seminal fluid, milk, milk whey, organ extracts, plant extracts, cell extracts, cell cultures (including cell lines), fermentation broths, serum, ascites fluid, and transgenic plant and animal extracts. As used herein, a biological fluid includes any treated or untreated fluid associated with living organisms, particularly blood, including whole blood, warm or cold blood, cord blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); blood products derived from blood or a blood component or derived from bone marrow; leukocytes, stem cells; red cells separated from plasma and resuspended in a physiological solution or a cryoprotective fluid; and platelets separated from plasma and resuspended in a physiological solution or a cryoprotective fluid. A biological fluid also includes a physiological solution comprising a bone marrow aspirate. The biological fluid may have been treated to remove some of the leukocytes before being used according to the invention. Blood product or biological fluid refers to the components described above, and to similar blood products or biological fluids obtained by other means and with similar properties.

In this context, a particularly preferred class of biological substances is immunoglobulins. The "immunoglobulins" category embraces whole immunoglobulins, including monoclonal and polyclonal antibodies, as well as Fab, $F(ab')_2$, $F_c$ and $F_v$ fragments, and other engineered antibody species. In an embodiment, the immunoglobulin may be immunoglobulin G (IgG). Alternatively, or additionally, one or more of any of the following: IgA, IgM, IgD and IgE, can be bound. In some embodiments, IgA and/or IgM are selectively bound.

Chromatographic separation according to embodiments of the invention can include, for example, substrates comprising chromatographic ion exchange resins, and hydrophobic interaction chromatography (HIC) resins, including, in some embodiments, those that can function under physiological pH and/or ionic strength. The substrate of the invention may be used to separate substances according to a variety of methods, including, for example, those disclosed in International Publication No. WO 2005/073711. A liquid sample containing one or more biological substances is contacted with an embodiment of the substrate of this invention for a period of time sufficient to allow at least one biological substance to bind to the substrate. Typically, the contact period is between about 30 seconds to about 12 hours.

An embodiment of a method of treating a sample comprising at least one biological substance comprises contacting an embodiment of the substrate with the sample for a period of time sufficient to allow at least one biological substance in the sample to bind to the substrate.

In another embodiment, a method for separating at least one substance from a liquid sample comprises contacting an embodiment of the substrate with a liquid sample comprising the at least one substance, wherein the substance adsorbs to the substrate; and adjusting the pH, ionic strength, or both, such that the substance desorbs from the substrate.

In an embodiment of the method, at least one substance comprises an antibody, for example, IgG, IgA, or a antibody fragment thereof.

In some embodiments of the method, the sample comprises a biological fluid, for example, but not limited to, plasma.

In one preferred embodiment of the method, the substrate is disposed in a column, and the method comprises passing the sample through the column.

If appropriate, the pH, ionic strength, or both, of the liquid sample may be adjusted prior to contacting the sample with the substrate. Additionally, or alternatively, the sample may be concentrated, diluted, or mixed with additives such as salts. Typical capture pH values for a range of proteins is from about 4 to about 10, although the capture pH can be higher or lower. Typically, a pH in the range of about 4 to about 8 promotes protein adsorption to those substrates that include a cation exchange moiety, while a pH in the range of about 6 to about 10 will accomplish the same where anion exchange moieties are used. In some embodiments, the substrate may bind proteins at a pH of about 5.5; or at a pH of about 7.2; or at a pH of about 8.0. However, the substrate can bind proteins at higher or lower pH.

The substrates of the invention are not limited by the ionic strength of the sample, and can be used with samples having low and high ionic strengths. Many biological substances will readily adsorb to the substrates at physiological ionic strength. Physiological ionic strength typically ranges from about 15 to about 20 mS/cm, although the ionic strength can be greater or lesser than those values. Typical salt concentrations that correspond to this range fall within about 0.1 to about 0.2 M, preferably 0.14 to about 0.17 M.

The temperature at which the liquid sample is contacted with the substrate varies between samples and a given chromatographic material as is known in the art. Preferably, the temperature is ambient, but it can be higher or lower than ambient.

After the sample is contacted with the substrate, the substrate is preferably washed with an equilibration buffer as is known in the art. An equilibration buffer is a buffer that is preferably of the pH at which the liquid sample was contacted with the substrate. Furthermore, the equilibration buffer washes from the substrate substances that do not adsorb to the substrate. Suitable equilibration buffers are known in the art, and include, for example, acetate buffer and phosphate buffered saline. The washing may be accomplished by bathing, soaking, or dipping the substrate with bound biological substance into the equilibration buffer. Alternatively, or additionally, the equilibration buffer may be rinsed, sprayed, or washed over the substrate.

The desired biological substance typically is one that adsorbs to the substrate. In other embodiments, the biological substance of interest may be removed in, for example, the equilibration buffer washing. In this case, the substance may be isolated from the buffer by methods known in the art. In another embodiment, the desired biological substance does not adsorb to the substrate, but the impurity to be removed does adsorb to the substrate. In this case, the desired biological substance may be recovered from the loading buffer or washing buffer by methods known in the art.

Biological substances that are adsorbed to the substrate are subsequently desorbed in one embodiment by adjusting the pH to a value where the substance desorbs. The pH at which desorption occurs will depend upon the substance and upon a given substrate. For example, for substrates that comprise an anion exchange moiety, desorption typically occurs over a pH gradient starting at about pH 8 and decreasing to about pH 3. For substrates that comprise a cation exchange moiety, the pH gradient applied typically starts at about pH 4 and is increased to about pH 11. For substrates that feature primarily hydrophobic groups, the pH gradient for desorption typically starts at about pH 7 and is decreased to about pH 3. For substrates that feature primarily hydrophobic groups, preferably an ionic strength gradient is also applied as described below. The pH can be adjusted by any routinely available reagent, such as aqueous solutions of Tris-HCl or carbonate buffers.

In some instances, as mentioned above, adjustment of the eluant ionic strength can increase effectiveness of the substrate. Thus, for substrates that comprise primarily hydrophobic groups, the ionic strength can be decreased concomitantly with pH. This is especially so for materials that additionally comprise —NH— moieties, which can give rise to mild ionic charges that become more effective as the ionic strength is decreased. The use of salt gradients is well-known in the art. Typically, salt concentrations for the present substrate need not exceed about 1.0 M, or about 0.5 M.

Typically, the desorbed biological substance is subsequently collected, and can be further processed if desired. Typical purities of biological substances, such as antibodies, that are purified in accordance with embodiments of the invention are about 70% or more, in some embodiments about 85% or more, and more preferably about 90% to about 99%.

In some embodiments, the substrate of the invention may be used to purify biological substances and simultaneously remove aggregates, allowing for one-step purification and aggregate removal. In some embodiments, the substrate preferentially binds biological substances, such as immunoglobulins (preferably monoclonal antibodies), while not binding aggregates. Thus, a sample comprising a biological substance to be purified may be contacted with the substrate, as described above; the biological substance will be adsorbed to the substrate; and the impurities and aggregates will pass through. The purified biological substance can subsequently be desorbed and collected as described above. In some embodiments, amounts of aggregates in the purified biological substance are less than, for example, about 10%, such as less than about 5%, or less than about 2%, or less than about 1%.

Many of the embodiments mentioned above comprise contacting a solution containing the biological substances with the substrate, and selectively adsorbing at least one biological substance in the solution by the substrate. In the event of the desired biological substance(s) being bound to the substrate, the elution of the latter allows it or them to be separated and collected in a purified and concentrated form. If the desired biological substance remains in the treated solution (the other biological substances being bound to the substrate) then the desired separation can be obtained directly by collecting the eluant.

Preferably, substrates according to embodiments of the invention can be regenerated repeatedly without degradation. Regeneration may be carried out by procedures known to those of skill in the art. For example, after use, the substrate may be contacted with a regeneration solution, such as aqueous sodium hydroxide. In an embodiment, the substrate is contacted with five column volumes of 1 M NaOH, for a minimum contact time of 30 minutes. Alternatively or additionally, the substrate may be contacted with an acid solution, such as aqueous hydrochloric acid or aqueous acetic acid. In an embodiment, the substrate is contacted with five column volumes of 0.1 M HCl or 0.1 M acetic acid, for a minimum contact time of 30 minutes. Alternatively or additionally, the substrate may be contacted with a salt solution, such as aqueous sodium chloride. In an embodiment, the substrate is contacted with five column volumes of 1 M NaCl, for a minimum contact time of 30 minutes. Before reuse, the substrate is preferably washed with equilibration buffer. The contact time and the composition and concentration of the regeneration solution(s) may be selected by one of skill in the art based on the nature of the ligand and the composition of the feedstock to ensure that the regeneration is efficient.

The illustrative separation methods described above can be used in a variety of techniques, including, for example, preparative methods employing fixed bed, fluidized bed, and batch chromatographies. Alternatively, the methods can be practiced in, for example, the context of high throughput separation techniques that utilize, for example, smaller devices such as spin columns or multiwell plate formats where device volumes can be as small as a few microliters.

When using batch adsorption/separation, the substrate can be added directly to the solution of biological substances, and the substrate/biological substance mixture is typically gently agitated for a time sufficient to allow the biological substances to bind to the substrate. The substrate, with adsorbed biological substances, may subsequently be removed by, for example, centrifugation or filtration, and the biological substances subsequently eluted from the substrate in a separate step.

In another embodiment, column chromatography may be used. In fixed bed column chromatography, the substrate is packed into a column, and the solution which contains the biological substances to be separated is applied to the substrate by pouring it through the substrate at a rate that allows the biological substances to bind to the substrate.

In fluidized bed column chromatography, a rising filtration flow and large/dense particles are used in order to maintain equilibrium against the rising forces. An essentially vertical column, typically composed of between 1 and 5 stages placed on top of the other, is used, and the solution successively passes through each stage and is drawn off by an overflow on the upper part of the upper stage. Preferably, the column has three stages. Each stage, with the exception of the uppermost one, is separated by two distribution systems, one distributing the solution at the base of the stage in question, the other distributing the solution towards the stage located immediately above.

In an embodiment, a column comprising the present substrate can be used in tandem with columns comprising other substrates, which would be effective in eliminating different impurities from a sample. Thus, one or more advantages of the present column can be viewed as being complementary to the characteristics of other or conventional columns. In this context, such a tandem arrangement of columns would conserve eluants and equilibration buffer, thereby reducing, if not eliminating, the need for additional sample manipulation and preparation.

The following examples further illustrate the invention but, of course, should not be construed as in any way limiting its scope.

EXAMPLE 1

This example demonstrates a process for synthesizing a ligand reagent methyl 2-(3-(tert-butoxycarbonylamino)-5-(isopropoyycarbonylamino)benzamido)acetate.

Glycine methyl ester hydrochloride (675 mg, 5 mmol) is dissolved in DMF (15 ml) and hydroxybenzotriazole (HOBt) (675 mg, 5 mmol), 3-(tert-butoxycarbonylamino)-5-(isopropoxycarbonylamino)benzoic acid (1.76 g, 5 mmol) are added. The reaction mixture is cooled to 0° C. and N,N'-diisopropylcarbodiimide (DIC) (1.54 mL, 10 mmol) is added slowly. The reaction mixture is further stirred at 0° C. for 5 minutes and at room temperature overnight. Water (100 ml) is added and stirring continues for an additional 20 minutes, followed by addition of ethyl acetate (100 ml). Crude product is stirred for an additional 5 minutes, and the organic layer is separated. The aqueous phase is further extracted with 2×70 ml ethyl acetate, and the combined organic phase is washed with water, dried with Na$_2$SO$_4$ and concentrated under vacuum.

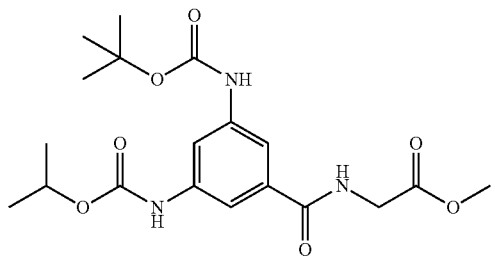 [SMILES: COC(=O)CNC(=O)c1cc(NC(=O)OC(C)C)cc(NC(=O)OC(C)(C)C)c1]

Column chromatography with silica gel in ethyl acetate/hexane 1:1 affords 1.65 g, 3.9 mmol white solid, 78% yield. $^1$H NMR (CDCl$_3$) δ: 7.72 (s, 1H, aromatic), 7.50 (s, 2H, aromatic), 6.50 (s, 1H, amide), 6.60 (s, 2H, amide), 4.22 (dd, 2H), 3.80 (s, 3H), 1.55 (s, 18H). LCMS (Ion mode: ESI) m/z [M-H$^+$] calcd. 422.20. found 422.00, [M+Na]$^+$466.07.

EXAMPLE 2

This example demonstrates a process for preparing a para-phenylenediamine (PDA) derivative of cellulose.

100 ml of a 50% slurry of cellulose beads are washed extensively with 1 M sodium hydroxide solution and then with water until neutral pH is obtained. To the drained 50 ml of beads are added 50 ml of sodium hydroxide solution at pH 11-12 and 5 ml of chloroacetic acid. The resultant mixture is then stirred for 24 h at 60° C. The reaction mixture is allowed to cool down to room temperature, washed to remove the unreacted chloroacetic acid and then neutralized.

The density of COOH was 60 μmol/ml of beads and is determined by acid-base titration for the attachment of various functionalities.

10 ml of the beads of carboxymethylcellulose at 60 μmol/ml of COOH is coupled with N-Boc-p-phenylenediamine (0.374 g, 1.8 mmol, 3 equivalents) in the presence of EDC (2.1 mmol) in 0.1M MES buffer at pH 4.7. The reaction mixture is washed to remove the excess of Boc-p-phenylenediamine and the side products. The BOC protecting group is removed with 3 M HCl to give the material shown below:

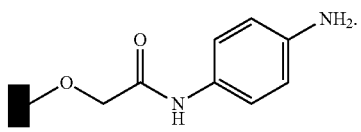

The product is white, and the density of the ligand was 40 μmol/ml of beads, determined by nitrogen elemental analysis. The product is stored at 4-8° C. as a 50% slurry in phosphate buffered saline (PBS) at pH 7.

EXAMPLE 3

This example demonstrates a process for preparing a para-phenylenediamine (PDA) derivative of cellulose with a sulfur-containing linker.

100 g of cross-linked cellulose beads, suction dried to a wet cake, are mixed with water (75 g), 32% NaOH (19.5 g), and allyl bromide (18.75 g). The mixture is tumbled for 24 hrs at room temperature.

The beads are extensively washed to remove the unreacted allyl bromide and byproducts, yielding allyl-cellulose as a substrate for the attachment of various functionalities.

100 g of allyl-cellulose beads, suction dried to a wet cake, are mixed with water (99 g) and 2-mercaptoacetic acid (1.0 g) at pH 11-12 and the mixture is tumbled for 48 h at room temperature. The resultant carboxyl derivative is washed to remove the side products, yielding acid-activated cellulose as a substrate for the attachment of various functionalities. The acid density is determined to be 90 µmol/ml of beads using elemental analysis.

10.0 ml of a 50% slurry of the obtained acid-activated bead is then condensed with (0.562 g, 2.7 mmol, 3 equivalents) of Boc-p-phenylenediamine in 0.1 M MES buffer at pH 4.7 in the presence of EDC (3 equivalents). The reaction mixture is shaken for 12 h at room temperature. The mixture is extensively washed to remove the unreacted Boc-p-phenylenediamine and the side products of the reaction. The BOC protecting group is removed with 3 M HCl to give the material shown below:

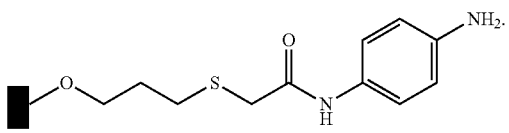

The product is white, and the density of the p-phenylenediamine ligand is 78 µmol/ml of beads, determined by nitrogen elemental analysis. The product can be stored at 4-8° C. as a 50% slurry in PBS buffer at pH 7.

EXAMPLE 4

This example demonstrates a process for preparing a meta-phenylenediamine derivative of cellulose with a sulfur-containing linker.

10 ml of a 50% slurry of acid-activated cellulose beads obtained according to the protocol described above in Example 3 is condensed with (0.562 g, 2.7 mmol, 3 equivalents) of N-Boc-m-phenylenediamine in 0.1 M MES buffer at pH 4.7 in the presence of EDC (3 equivalents). The BOC protecting group is removed with 3 M HCl to give the material shown below:

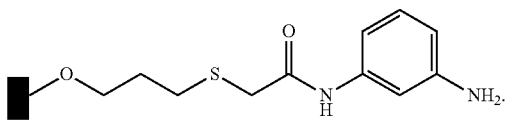 [SMILES: COCCCSCC(=O)Nc1cccc(N)c1]

The product is white. The ligand density is 62 µmol/ml of beads, determined by nitrogen elemental analysis. The product can be stored at 4-8° C. as a 50% slurry in PBS buffer at pH 7.

The same product is prepared by coupling m-phenylenediamine instead of N-Boc-m-phenylenediamine, and the ligand density is 64 µmol/ml of beads.

EXAMPLE 5

This example demonstrates a process for preparing an ortho-phenylenediamine derivative of cellulose with a sulfur-containing linker.

10 ml of a 50% slurry of acid-activated cellulose beads obtained according to the protocol described above in Example 3 is condensed with (0.562 g, 2.7 mmol, 3 equivalents) of Boc-o-phenylenediamine in 0.1 M MES buffer at pH 4.7 in the presence of EDC (3 equivalents). The reaction mixture is shaken for 24 h at room temperature. The mixture is extensively washed to remove the unreacted Boc-o-phenylenediamine and the side products of the reaction. The BOC protecting group is removed with 3 M HCl to give the material shown below:

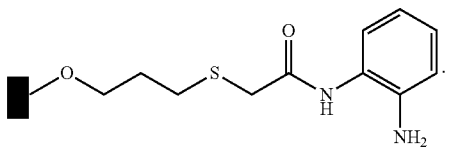 [SMILES: COCCCSCC(=O)Nc1ccccc1N]

The product is white and the ligand density was 40 µmol/ml of beads, determined by elemental analysis. The product is stored as a 50% slurry in PBS buffer at pH 7.

EXAMPLE 6

This example demonstrates a process for preparing a 4,6-diaminopyrimidine derivative of cellulose with a sulfur-containing linker.

10 ml of a 50% slurry of acid-activated cellulose beads obtained according to the protocol described above in Example 3 is condensed with (0.395 g, 2.7 mmol, 3 equivalents) of 4,6-diaminopyrimidine hydrochloride in 0.1 M MES buffer at pH 4.7 in the presence of EDC (3 equivalents) for 12 h at room temperature. The product is washed to remove the unreacted 4,6-diaminopyrimidine and the side products.

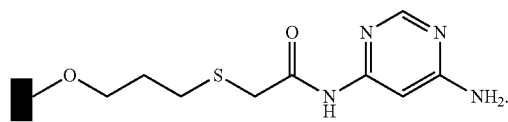 [SMILES: COCCCSCC(=O)Nc1cc(N)ncn1]

The beads derivatized with the 4,6-diaminopyrimidine are white. The ligand density is determined to be 30 µmol/ml of beads. The beads can be stored at 4-8° C. as a 50% slurry in PBS buffer at pH 7.

EXAMPLE 7

This example demonstrates a process for preparing a 2,4,6-triaminopyrimidine derivative of cellulose with a sulfur-containing linker.

10 ml of a 50% slurry of acid-activated cellulose beads obtained according to the protocol described above in Example 3 is washed thoroughly with water to remove the storage solution and then with 0.1 M MES buffer at pH 4.7. Afterwards, the beads are mixed with 3.5 mmol 2,4,6-triaminopyrimidine dissolved in 0.1 M MES (3 ml) and 2 M HCl (1.75 ml), followed by addition of EDC (1.5 mmol). The reaction mixture is tumbled at room temperature for three hours, and cleaned extensively to remove unreacted reagents and side products.

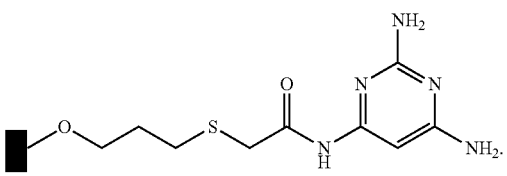 [SMILES: COCCCSCC(=O)Nc1cc(N)nc(N)n1]

The product is white with a ligand density of 30 μmol/ml of beads, determined by elemental analysis. The product is stored as a 50% slurry in PBS buffer at pH 7.

EXAMPLE 8

This example demonstrates a process for preparing a 1,5-diaminonaphthalene derivative of cellulose with a sulfur-containing linker.

10 ml of a 50% slurry of acid-activated cellulose beads obtained according to the protocol described above in Example 3 is condensed with (0.427 g, 2.7 mmol, 3 equivalents) of 1,5-diaminonaphthalene in a mixture of methanol and 0.1 M MES buffer at pH 4.7 in the presence of EDC (3 equivalents) for 12 h at room temperature. The product is then washed extensively to remove unreacted diamine and side products.

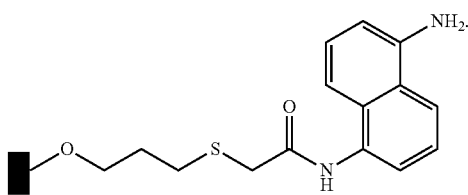 [SMILES: COCCCSCC(=O)Nc1cccc2c(N)cccc12]

The beads derivatized by 1,5-diaminonaphthalene are off-pink. The ligand density is determined by elemental analysis to be 41 μmol/ml of beads. The product is stable and can be stored at 4-8° C. as a 50% slurry in PBS buffer at pH 7.

EXAMPLE 9

This example demonstrates a process for preparing a 2,5-diaminopyridine derivative of cellulose with a sulfur-containing linker.

10 ml of a 50% slurry of acid-activated cellulose beads obtained according to the protocol described above in Example 3 is condensed with (0.491 g, 3 mmol, 3 equivalents) 2,5-diaminopyridine dihydrochloride in 0.1 M MES buffer at pH 4.7 in the presence of EDC (5 equivalents). The product is extensively washed to remove unreacted reagents and side

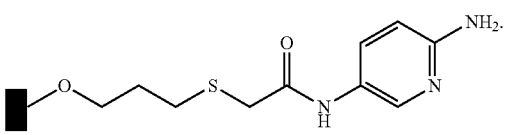 [SMILES: COCCCSCC(=O)Nc1ccc(N)nc1]

The beads derivatized with the 2,5-diaminopyridine are white. The ligand density is 58 μmol/ml of beads, determined by elemental analysis. The product can be stored at 4-8° C. as a 50% slurry in PBS buffer at pH 7.

EXAMPLE 10

This example demonstrates a process for preparing a 2,4,6-trimethyl-1,3-benzenediamine derivative of cellulose with a sulfur-containing linker.

10 ml of a 50% slurry of acid-activated cellulose beads obtained according to the protocol described above in Example 3 is condensed with (0.405 g, 2.7 mmol, 3 equivalents) of 2,4,6-trimethyl-1,3-benzenediamine in a mixture of methanol and 0.1 M MES buffer at pH 4.7 in the presence of EDC (3 equivalents). The product is washed to remove side products and the unreacted reagents.

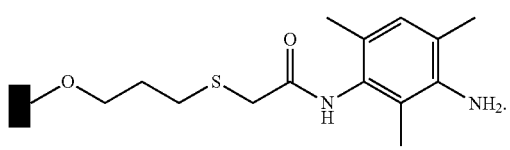

The beads derivatized with 2,4,6-trimethyl-1,3-benzenediamine are white. The ligand density is 72 μmol/ml of beads, determined by elemental analysis.

EXAMPLE 11

This example demonstrates a process for preparing a tetramethyl-p-phenylenediamine derivative of cellulose with a sulfur-containing linker.

10 ml of a 50% slurry of acid-activated cellulose beads obtained according to the protocol described above in Example 3 is washed thoroughly with water to remove storage solution and then with 0.1 M MES buffer at pH 4.7. 2,3,5,6-tetramethyl-1,4-phenylenediamine (4.0 mmol) dissolved in methanol (4 ml) is added, followed by the addition of EDC (4.0 mmol) dissolved in 0.1 M MES to the beads. The beads are tumbled overnight and washed extensively to remove excess diamine and side products.

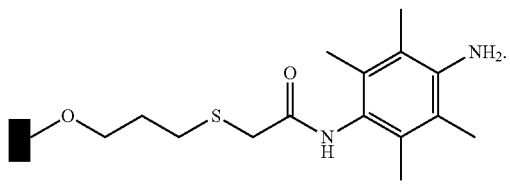 [SMILES: COCCCSCC(=O)Nc1c(C)c(C)c(N)c(C)c1C]

The product is white with a ligand density of 65 μmol/ml of beads, determined by elemental analysis. The product is stored as a 50% slurry in PBS buffer at pH 7.

EXAMPLE 12

This example demonstrates a process for preparing a 3,5-diaminobenzoic acid derivative of cellulose with a sulfur-containing linker.

10 ml of a 50% slurry of acid-activated cellulose beads obtained according to the protocol described above in Example 3 is condensed with (0.486 g, 2.7 mmol, 3 equivalents) of the ethyl ester of 3,5-diaminobenzoic acid in a 1:1 mixture of methanol and 0.1 M MES buffer at pH 4.7 in the presence of EDC (3 equivalents). Saponification is then carried out using 1 M NaOH at room temperature for 12 h to yield the product shown below:

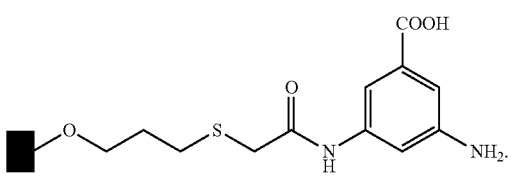 [SMILES: COCCCSCC(=O)Nc1cc(N)cc(C(=O)O)c1]

The beads derivatized with this diaminobenzoic acid are off-white. The ligand density is 40 μmol/ml of beads, determined by elemental analysis.

EXAMPLE 13

This example demonstrates a process for preparing a 2-methoxy-5-tert-butyl-1,3-benzenediamine derivative of cellulose with a sulfur-containing linker.

10 ml of a 50% slurry of acid-activated cellulose beads obtained according to the protocol described above in Example 3 is washed thoroughly with water to remove the storage solution and then with 0.1 M MES buffer at pH 4.7. 4-tert-butyl-2,6 diaminoanisole (4.0 mmol) dissolved in methanol (4 ml) is added, followed by the addition of EDC (4.0 mmol) dissolved in 0.1 M MES. The beads are tumbled overnight and washed extensively to remove excess diamine and side products.

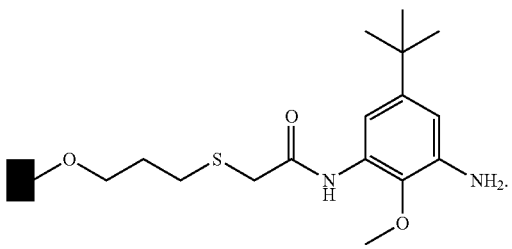 [SMILES: COCCCSCC(=O)Nc1cc(C(C)(C)C)cc(N)c1OC]

The product is white and can be stored as a 50% slurry in PBS buffer at pH 7.

EXAMPLE 14

This example demonstrates a process for preparing a 2,6-diaminopyridine derivative of cellulose with a sulfur-containing linker.

5.0 ml of a 50% slurry of acid-activated cellulose beads obtained according to the protocol described above in Example 3 is washed thoroughly with water to remove the storage solution and then with 0.1 M MES buffer at pH 4.7. The beads are mixed with 2,6-diaminopyridine (382 mg, 3.5 mmol) dissolved in 0.1 M MES (2 ml) and 2 M HCl (1.75 ml). EDC (306 mg, 1.6 mmol) dissolved in 0.1 M MES (1.5 ml) was added. The beads are tumbled overnight at room temperature and washed extensively to remove unreacted reagents and side products.

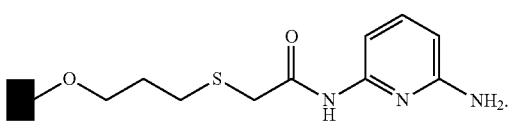 [SMILES: COCCCSCC(=O)Nc1cccc(N)n1]

Density of the coupled ligand is determined to be 26 μmol/ml of wet beads by elemental analysis. The product is white and can be stored as a 50% slurry in PBS buffer at pH 7.

EXAMPLE 15

This example demonstrates a process for preparing a 4-nitro-1,2-phenylendiamine derivative of cellulose with a sulfur-containing linker.

6.0 ml of a 50% slurry of acid-activated cellulose beads obtained according to the protocol described above in Example 3 is washed thoroughly with water to remove the storage solution and then with 0.1 M MES buffer at pH 4.7. 4-nitro-1,2-phenylendiamine (2.4 mmol) dissolved in methanol (4 ml) is added, followed by addition of EDC (2.4 mmol, 458 mg) dissolved in 0.1 M MES (2 ml). The beads are tumbled overnight and washed extensively to remove unreacted reagents and side products.

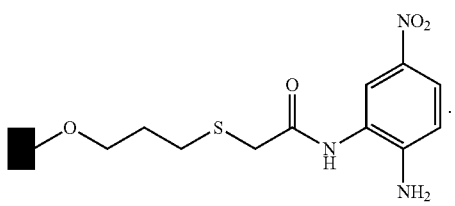 [SMILES: COCCCSCC(=O)Nc1cc([N+](=O)[O-])ccc1N]

The final product is orange and can be stored as a 50% slurry in PBS buffer at pH 7.

EXAMPLE 16

This example demonstrates a process for preparing a 4,5,6-triaminopyrimidine derivative of cellulose with a sulfur-containing linker.

5.0 ml of a 50% slurry of acid-activated cellulose beads obtained according to the protocol described above in Example 3 is washed thoroughly with water to remove the storage solution and then with 0.1 M MES buffer at pH 4.7. 4,5,6-triaminopyrimidine sulfate (3.2 mmol, 702 mg) suspended in 0.1 M MES (4 ml) is added, followed by addition of EDC (1.5 mmol, 280 mg) dissolved in 0.1 M MES (1 ml). The reaction mixture is tumbled for three hours and washed extensively to remove unreacted reagents and side products.

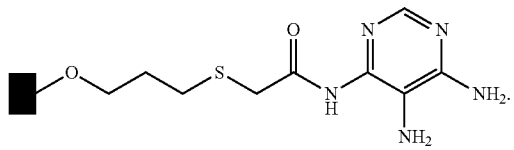 [SMILES: COCCCSCC(=O)Nc1ncnc(N)c1N]

The final product is white and can be stored as a 50% slurry in PBS buffer at pH 7.

EXAMPLE 17

This example demonstrates a process for preparing a 4-chloro-2,6-diaminopyridine derivative of cellulose with a sulfur-containing linker.

5.0 ml of a 50% slurry of acid-activated cellulose beads obtained according to the protocol described above in Example 3 is washed thoroughly with water to remove the storage solution and then with 0.1 M MES buffer at pH 4.7.

The beads are mixed with 4-chloro-2,6-diaminopyridine (3.5 mmol) dissolved in 0.1 M MES (3 ml) and 2 M HCl (1.75 ml), followed by addition of EDC (1.5 mmol). The reaction mixture is then tumbled at room temperature for three hours, and washed extensively to remove unreacted reagents and side products.

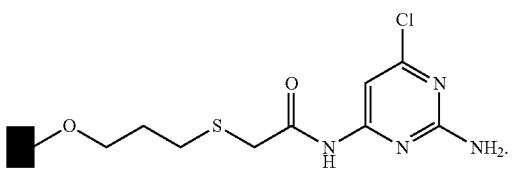 [SMILES: COCCCSCC(=O)Nc1cc(Cl)nc(N)n1]

The final product is white and can be stored as a 50% slurry in PBS buffer at pH 7.

EXAMPLE 18

This example demonstrates a process for preparing a 2,4-diaminopyrimidine derivative of cellulose with a sulfur-containing linker.

10.0 ml of a 50% slurry of acid-activated cellulose beads obtained according to the protocol described above in Example 3 is washed thoroughly with water to remove the storage solution and then with 0.1 M MES buffer at pH 4.7. The beads are then mixed with 2,4-diaminopyrimidine (7.0 mmol) dissolved in 0.1 M MES (6 ml) and 2 M HCl (3.5 ml), followed by addition of EDC (3.0 mmol). The reaction mixture is tumbled at room temperature for three hours, and washed extensively to remove excess reagents and side

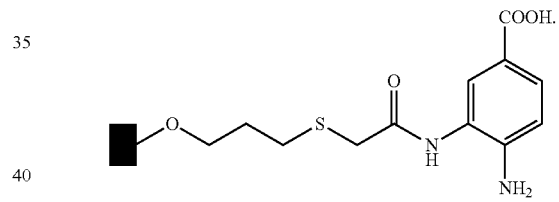

The final product is white and can be stored as a 50% slurry in PBS buffer at pH 7.

EXAMPLE 19

This example demonstrates a process for preparing a 2,5-diaminobenzene sulfonic acid derivative of cellulose with a sulfur-containing linker.

5.0 ml of a 50% slurry of acid-activated cellulose beads obtained according to the protocol described above in Example 3 is washed thoroughly with water to remove the storage solution and then with 0.1 M MES buffer at pH 4.7.

The beads are then mixed with 2,5-diaminobenzene sulfonic acid (300 mg, 1.6 mmol) dissolved in 0.1 M MES (3 ml) and 1 M NaOH (1.5 ml), followed by addition of EDC (306 mg, 1.6 mmol) dissolved in 0.1 M MES (2 ml). The beads are tumbled at room temperature for 24 hours and washed extensively to remove excess reagents and side products.

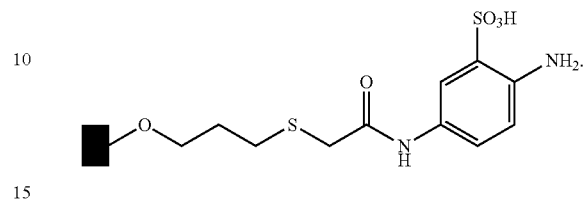

The density of the ligand is determined to be 28 μmol/ml of beads by elemental analysis. The final product can be stored as a 50% slurry in PBS buffer at pH 7.

EXAMPLE 20

This example demonstrates a process for preparing a 3,4-diaminobenzoic acid derivative of cellulose with a sulfur-containing linker.

10 ml of a 50% slurry of acid-activated cellulose beads obtained according to the protocol described above in Example 3 is condensed with (0.486 g, 2.7 mmol, 3 equivalents) of the ethyl ester of 3,4-diaminobenzoic acid in a 1:1 mixture of methanol and 0.1 M MES buffer at pH 4.7 in the presence of EDC (3 equivalents). Saponification is then carried out using 1 M NaOH at room temperature for 12 h to yield the product shown below:

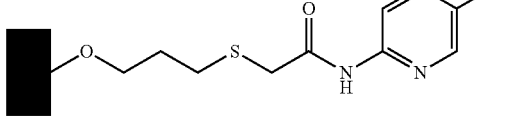

The beads derivatized with this diaminobenzoic acid are off-white. The ligand density is 70 μmol/ml of resin, determined by elemental analysis.

Examples 21-45

Cellulose derivatives with sulfur-containing linkers and ligands as shown in Table 1, below, are prepared according to the protocol described in Example 8, substituting the appropriate ligand reagents for the 2,5-diaminobenzene sulfonic acid in Example 19.

TABLE 1

| Example | Ligand |
|---------|--------|
| 21 | 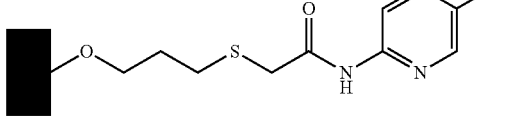 |

TABLE 1-continued

| Example | Ligand |
|---|---|
| 22 | |
| 23 | |
| 24 | |
| 25 | |
| 26 | |
| 27 | |

TABLE 1-continued

| Example | Ligand |
|---|---|
| 28 | |
| 29 | |
| 30 | |
| 31 | |
| 32 | |
| 33 | |

TABLE 1-continued
| Example | Ligand |
|---|---|
| 34 | 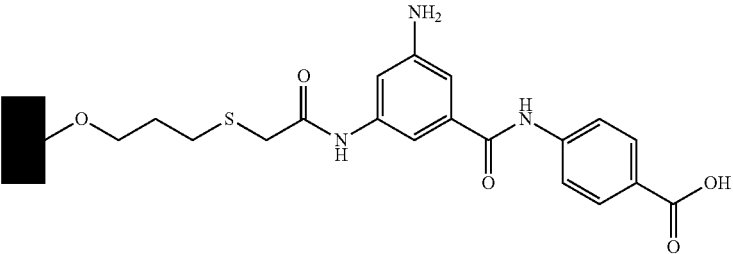 [SMILES: Nc1cc(NC(=O)CSCCCOC2CCCCC2)cc(C(=O)Nc2ccc(C(=O)O)cc2)c1] |
| 35 | 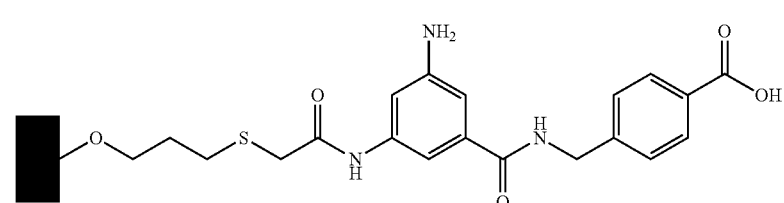 |
| 36 | 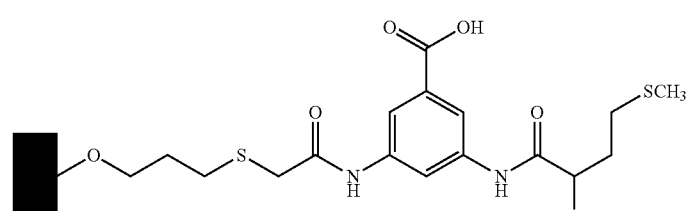 |
| 37 | 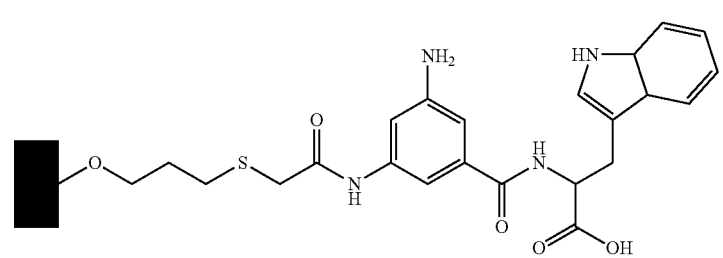 [SMILES: Nc1cc(NC(=O)CSCCCOC2CCCCC2)cc(C(=O)NC(CC2=CNC3C=CC=CC23)C(=O)O)c1] |
| 38 | 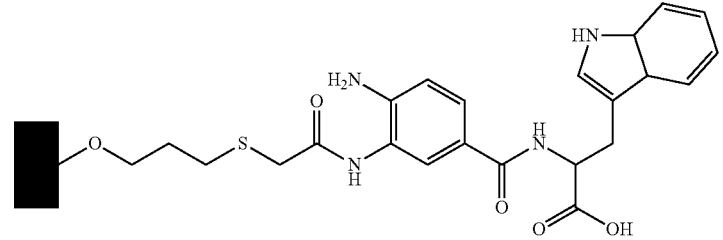 [SMILES: Nc1ccc(C(=O)NC(CC2=CNC3C=CC=CC23)C(=O)O)cc1NC(=O)CSCCCOC1CCCCC1] |
| 39 | 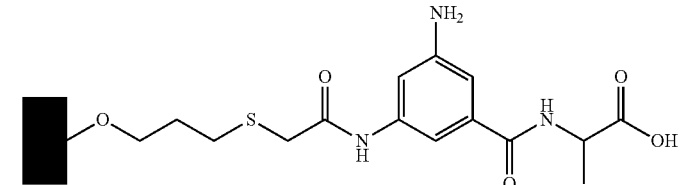 |

TABLE 1-continued
| Example | Ligand |
|---|---|
| 40 | 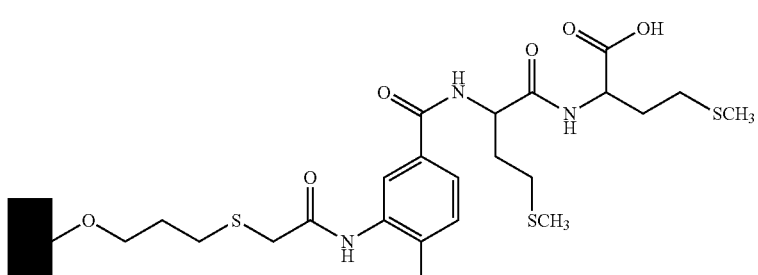 |
| 41 | 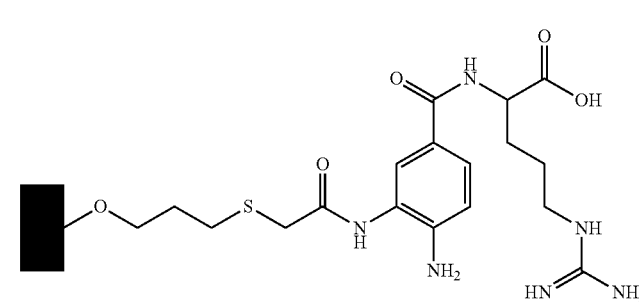 [SMILES: N=C(N)NCCCC(NC(=O)c1ccc(N)c(NC(=O)CSCCCOC2CCCCC2)c1)C(=O)O] |
| 42 | 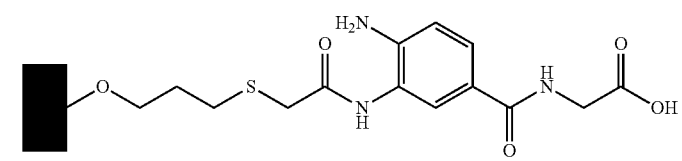 [SMILES: Nc1ccc(C(=O)NCC(=O)O)cc1NC(=O)CSCCCOC1CCCCC1] |
| 43 | 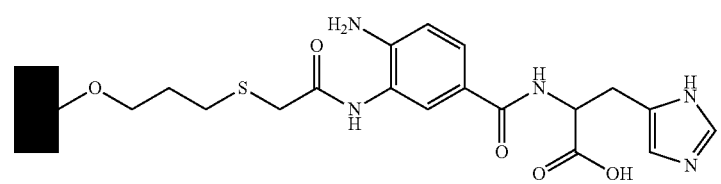 [SMILES: Nc1ccc(C(=O)NC(Cc2cnc[nH]2)C(=O)O)cc1NC(=O)CSCCCOC1CCCCC1] |
| 44 | 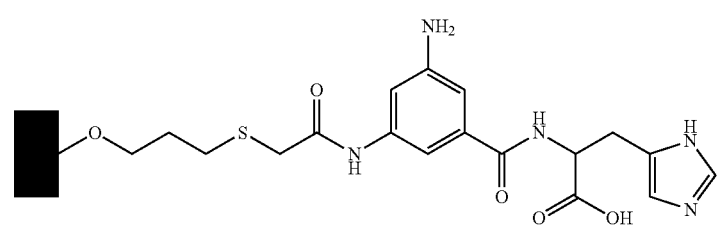 [SMILES: Nc1cc(NC(=O)CSCCCOC2CCCCC2)cc(C(=O)NC(Cc2cnc[nH]2)C(=O)O)c1] |
| 45 | 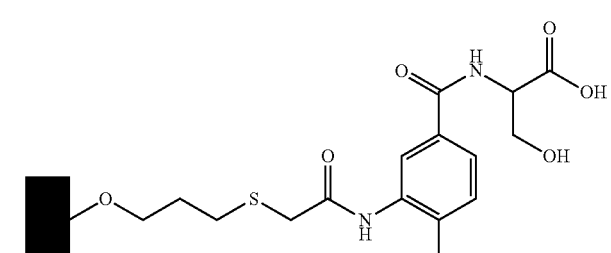 |

EXAMPLE 46

This example demonstrates a method for isolating and purifying IgG from crude human plasma using a solid substrate according to an embodiment of the invention.

A 1-ml column is packed with the solid substrate prepared according to Example 3. The solid substrate is equilibrated with a 20 mM phosphate buffer at pH 7.2.

Next, a sample of 10 ml of crude human plasma is diluted 1:1 in equilibration buffer, filtered through 0.2 μm membrane, and 12 ml are loaded directly onto the column. The column is then washed with 20 mM phosphate buffered 0.5 M NaCl at pH 7.2, to ensure the elimination of non-adsorbed proteins. Bound impurities are removed by washing the column with 20 mM phosphate buffer at pH 7.2.

The desired IgG is eluted with 20 mM acetate buffer at pH 4.0. 25 mg of IgG is collected and its purity was estimated to be >99%.

EXAMPLE 47

This example demonstrates a method for isolating and purifying IgG from plasma using a solid substrate according to another embodiment of the invention.

A 1-ml column is packed with the solid substrate prepared according to Example 9. The solid substrate is equilibrated with a 20 mM phosphate buffer at pH 7.4.

Next, a sample of 10 ml of human plasma is diluted 1:1 in equilibration buffer, filtered through a 0.2 μm membrane, and 20 ml are loaded directly onto the column. The column is then washed with 20 mM phosphate buffered 0.15 M NaCl at pH 7.2, to ensure the elimination of non-adsorbed proteins. Bound impurities are removed by washing the column with 20 mM phosphate buffer at pH 7.2.

The desired IgG is eluted with 20 mM sodium acetate buffer at pH 5.0. 35 mg of the desired IgG is collected and its purity was estimated to be >99%.

EXAMPLE 48

This example demonstrates that good dynamic binding capacity can be achieved with varying ligand densities using substrates according to embodiments of the invention.

Solid substrates are prepared according to Example 3, except that the coupling conditions of p-phenylenediamine with the acid-activated beads (changing the stoichiometry of phenylenediamine and EDC versus acid density) are varied to produce samples with varying ligand density.

IgG dynamic protein binding capacity (DBC) for each substrate sample is determined on an ÄKTA Explorer 100 LC Workstation (GE Healthcare Biosciences, Pittsburgh, Pa.) in accordance with the UNICORN software instructions. Equilibration and washing flow rates are 1 ml/min, and the loading flow rate is 0.33 ml/min (3 min residence time). Human IgG is loaded to 50% breakthrough (BT). HR 5/5 column (5 mm diameter and 5 cm length, volume=1 ml) from Amersham 18-0383-01 is used for resin packing, and A280 reading is determined using UltraSpec 1000. Commercial IgG (SeraCare Life Sciences, lot number G111RM-25B0802) at a concentration of 2.0 mg/ml is used. Loading buffer for IgG is in 20 mM $NaH_2PO_4$ at pH 7.2 and equilibration and washing buffer is also in $NaH_2PO_4$, 20 mM at pH 7.2. Elution buffer is 0.1 M acetic acid, pH 3.1. Dynamic binding capacity from elution is calculated by measuring the amount of protein in all elution fractions. Recovery is calculated using the amount of protein in the elution divided by the protein actually bound to the column (the amount of protein bound to the column=amount of protein loaded to the column—protein in the breakthrough and wash). Binding capacity at 10% breakthrough is calculated using the equation: (protein concentration in load)*$(V_{10\% \, BT} - V_{void})$. The void volume of the system and column is measured by injection of 1% acetone.

The ligand density and dynamic binding capacity of one substrate sample are shown in FIG. 1. The substrate tested shows good dynamic binding capacity even at low ligand densities of about 50 μmol/ml or greater.

EXAMPLE 49

This example demonstrates that ligand density can be varied while still obtaining pure IgG using substrates according to embodiments of the invention.

Solid substrates are prepared according to Example 3 except that the coupling conditions of p-phenylenediamine with the acid-activated beads (changing the stoichiometry of phenylenediamine and EDC versus acid density) are varied to produce samples with varying p-phenylenediamine (PDA) ligand density. Each solid substrate sample is loaded into a separate column and used to purify IgG from human plasma as described in Example 46.

Figure 2:
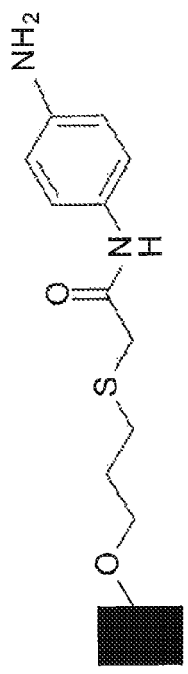
FIG. 2 is a graph showing varying ligand density and obtaining pure IgG using a substrate with a para-phenylenediamine (PDA) ligand according to an embodiment of the invention.
Figure 2:
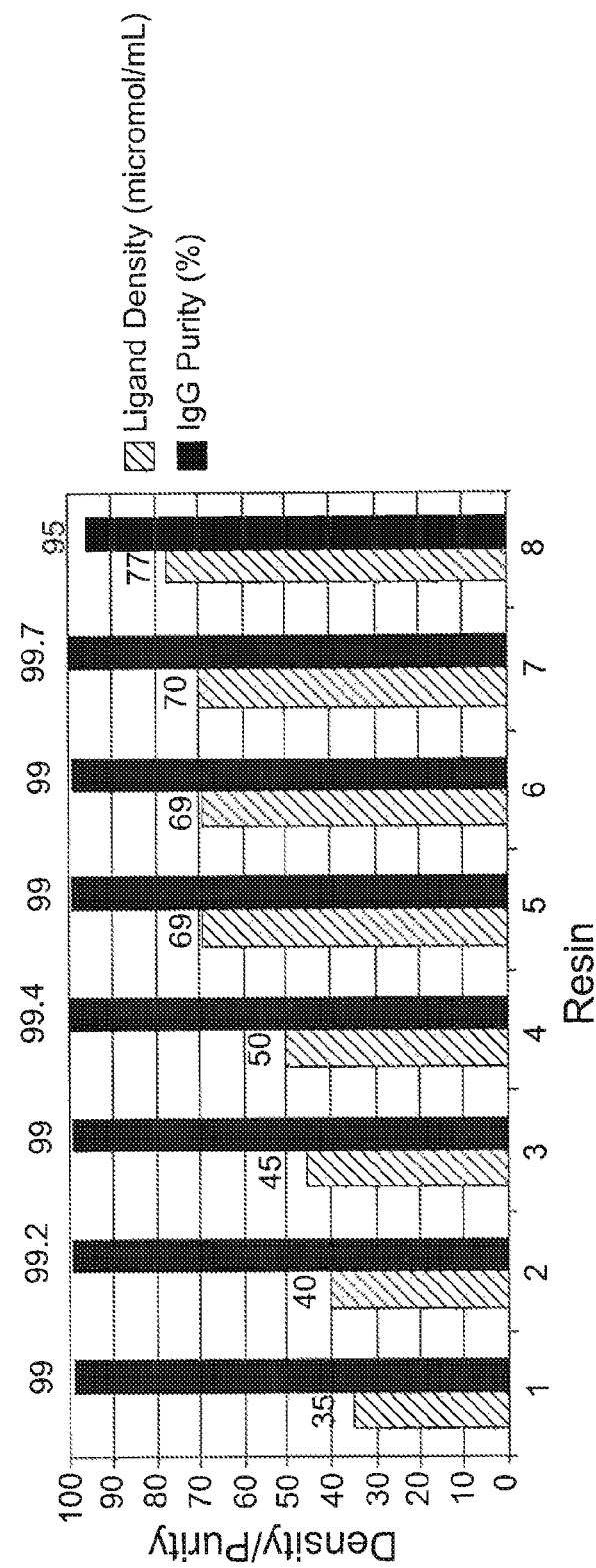

The IgG purity obtained from each substrate sample is shown in FIG. 2. Even at ligand densities as low as 35 μmol/ml, IgG is obtained with purity of 99%. No significant increase in IgG purity with ligand density is observed for substrates having ligand densities of 35 μmol/ml or greater.

EXAMPLE 50

This example demonstrates IgG binding versus residence time using substrates according to embodiments of the invention.

Solid substrates are prepared according to Example 3. Each solid substrate sample is loaded into a separate column and used to bind pure IgG according to the following procedure: IgG 2 mg/ml in phosphate buffer at pH 7.2 and a conductivity of 6 mS/cm is loaded to each column until the 50% BT is reached. The column is then washed with 0.5 M NaCl to remove IgG adsorbed to the beads. The IgG is then eluted using 0.1 M acetic acid buffer at pH 3.1.

The amount of IgG bound and eluted at 10% breakthrough, along with the percent recovery at pH 3, for each residence time tested is shown in Table 2. The substrate exhibits high binding capacity at 6 minutes residence time, and the recovery of IgG is high for various residence times.

TABLE 2

| Residence time (min) | Bound (mg/ml) | Eluted (mg/ml) | Recovery (%) |
|---|---|---|---|
| 3 | 24.4 | 23.5 | 96.3 |
| 4 | 31.0 | 29.6 | 95.5 |
| 6 | 40.9 | 37.7 | 92.3 |

EXAMPLE 51

This example demonstrates the effect of pH on IgG binding and recovery using substrates according to embodiments of the invention.

Solid substrates were prepared according to Example 12. Each solid substrate sample was loaded into a separate column and used to purify IgG from human plasma according to the following procedure: IgG 2 mg/ml in various buffer solutions with variable pH (5-8.5) (see Table 2) and a conductivity of 6 mS/cm was loaded to each column until the 10% BT was reached. The column was then washed with 0.5 M NaCl to remove IgG adsorbed to the beads. The IgG was then eluted using 0.1 M acetic acid buffer at pH 3.1.

The amount of IgG bound and eluted at 10% breakthrough, along with the percent recovery, for each pH value tested is shown in Table 3. At all pH values tested, at least 98.8% of the IgG bound was recovered. pH 5.5 is the optimum loading pH for this ligand.

TABLE 3

| pH | IgG bound at 10% BT | IgG eluted at 10% BT | Recovery (%) |
| --- | --- | --- | --- |
| 5.0 | 19.2 | 19.2 | 100 |
| 5.5 | 25 | 24.8 | 99 |
| 6.0 | 24.3 | 24.0 | 98.8 |
| 7.2 | 19.1 | 19.0 | ~100 |
| 8.5 | 3 | 3 | 100 |

EXAMPLE 52

This example demonstrates reuse of substrates for IgG purification from crude human plasma using substrates according to embodiments of the invention.

A solid substrate is prepared according to Example 3 and is loaded into a column and used to treat a sample of biological material comprising IgG according to the procedure described in Example 46. Following elution, the solid substrate is regenerated using 1 M NaOH at a flow rate of 1 ml/minute and again used to treat a sample of biological material comprising IgG according to the same procedure. The regeneration and reuse cycle is repeated a second time, for three total treatments of biological samples.

The amount of IgG binding and purity for each cycle is shown in Table 4. The substrate produces IgG of high purity even after repeated uses.

TABLE 4

| Test # | Residence time (min) | Binding from elution (mg/ml) | Purity (%) |
| --- | --- | --- | --- |
| 1 | 3 | 25.1 | 98.3 |
| 2 | 3 | 22.0 | 99.4 |
| 3 | 6 | 23.0 | 99.7 |

EXAMPLE 53

This example demonstrates IgG purification from crude human plasma (3 minutes residence time) using substrates according to embodiments of the invention.

Solid substrates are prepared according to Examples 3, 4, 9, 10, and 11. Each solid substrate sample is loaded into a separate column and used to purify IgG from human plasma as described in Example 46.

The amount of IgG eluted and purity for each substrate tested is shown in Table 5. All substrates tested yield IgG of high purity.

TABLE 5

| Ligand | IgG elution from crude human plasma | Purity (%) |
| --- | --- | --- |
| 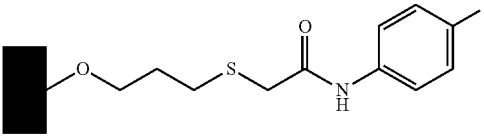 | 25.5 mg/ml of resin | >99 |
| 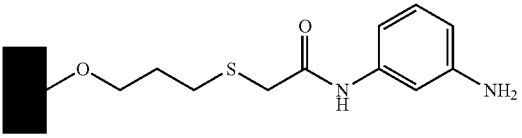 [SMILES: Nc1cccc(NC(=O)CSCCCOC2CCCCC2)c1] | 20 mg/ml of resin | 91 |
| 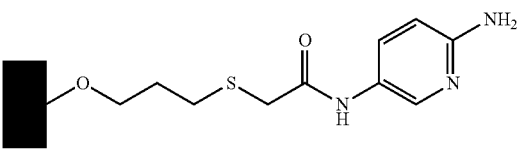 [SMILES: Nc1ccc(NC(=O)CSCCCOC2CCCCC2)cn1] | 35 mg/ml of resin | >99 |
| 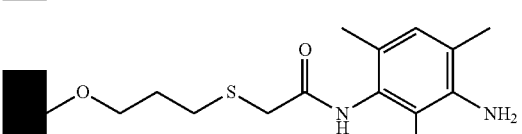 | 9 mg/ml of resin | >99 |
| 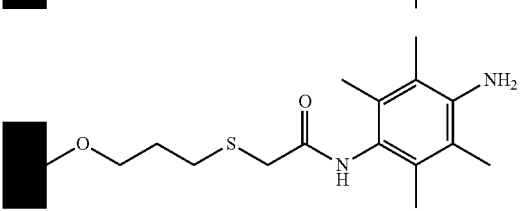 | 3 mg/ml of resin | >99 |

EXAMPLE 54

This example demonstrates pure IgG binding and recovery at 10% breakthrough. (3 minutes residence time) using substrates according to embodiments of the invention.

Solid substrates are prepared according to Examples 3, 10, 11, and 13. Each solid substrate sample is loaded into a separate column and used to bind pure IgG as described in Example 50.

The amount of IgG bound and eluted at 10% breakthrough and 3 minutes residence time, along with the percent recovery, for each substrate is shown in Table 6.

TABLE 6

| Ligand | Bound (mg/ml) | Elution (mg/ml) | Recovery (%) |
|---|---|---|---|
| 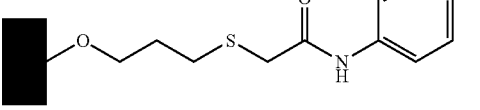 | 24.9 | 23.7 | 95 |
| 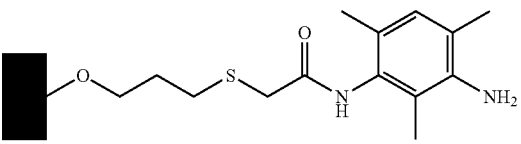 [SMILES: Cc1cc(C)c(NC(=O)CSCCCOC2CCCCC2)c(C)c1N] | 26.4 | 24.2 | 91.3 |
| 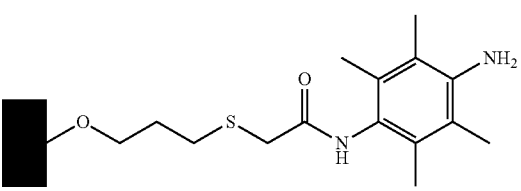 [SMILES: Cc1c(C)c(NC(=O)CSCCCOC2CCCCC2)c(C)c(C)c1N] | 21.5 | 19.8 | 92.3 |
| 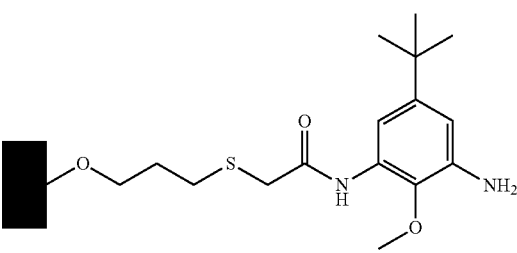 [SMILES: COc1c(N)cc(C(C)(C)C)cc1NC(=O)CSCCCOC1CCCCC1] | 10 | 3.5 | 57 |

EXAMPLE 55

This example demonstrates Fab binding and recovery at 10% breakthrough using substrates according to embodiments of the invention.

Solid substrates are prepared according to Examples 3, 4, 5, and 8. Each solid substrate sample is loaded into a separate column and used to bind pure Fab under the following conditions: 0.5 mg/ml solution of Fab in 100 mM Tris-HCl, 10 mM EDTA buffer at pH 7.4 is loaded onto each column until 10% breakthrough is reached. The columns are then washed with the equilibration buffer (100 mM Tris-HCl and 10 mM EDTA at pH 7.4), and the Fab is eluted with 300 mM glycine buffer at pH 3.

The Fab dynamic binding capacity (DBC) at 10% breakthrough and 3 minutes residence time, along with the percent recovery for each substrate is shown in Table 7.

TABLE 7

| Ligand | DBC (mg/ml) | Recovery (%) |
|---|---|---|
| ■—O—CH₂CH₂CH₂—S—CH₂—C(=O)—NH—C₆H₄—NH₂ (para) | 10 | 83 |
| ■—O—CH₂CH₂CH₂—S—CH₂—C(=O)—NH—C₆H₄—NH₂ (meta) | 24 | 81 |
| ■—O—CH₂CH₂CH₂—S—CH₂—C(=O)—NH—C₆H₄—NH₂ (ortho) | 0.4 | 90 |
| ■—O—CH₂CH₂CH₂—S—CH₂—C(=O)—NH-naphthyl-NH₂ | 23 | 55 |

EXAMPLE 56

This example demonstrates monoclonal antibody binding versus residence time using substrates according to embodiments of the invention.

A solid substrate is prepared according to Example 3 and is loaded into a column and used to bind pure monoclonal antibodies according to the following procedure: 2 mg/ml of mAb in sodium phosphate buffer at pH 7.2 with a conductivity of 6 mS/cm is loaded onto each column until it reaches 10% breakthrough at various residence times. The column is washed with 20 mM sodium phosphate buffer and 500 mM NaCl, and the mAb is eluted with 20 mM sodium acetate at pH 4.0.

The amounts of monoclonal antibodies binding to the substrate and eluted from the substrate as well as the percent recovery are shown in Table 8. The substrate exhibits high recovery of monoclonal antibodies at short residence times.

TABLE 8

| Residence time (min) | Bound (mg/ml) | Eluted (mg/ml) | Recovery (%) |
|---|---|---|---|
| 3 | 41.0 | 40.3 | 98.2 |
| 4 | 46.7 | 46.5 | 99.6 |
| 6 | 62.0 | 58.3 | 94.0 |

EXAMPLE 57

This example demonstrates monoclonal antibody binding versus residence time using substrates according to embodiments of the invention.

A solid substrate is prepared according to Example 20 and is loaded into a column and used to bind pure monoclonal antibodies according to the following procedure: 2 mg/ml of mAb in sodium phosphate plus 150 mM NaCl at pH 5.5 with a conductivity of 15 mS/cm is loaded onto each column until it reaches 10% breakthrough at various residence times. The column is washed with 20 mM sodium phosphate plus 150 mM NaCl (with a conductivity of 15 mS/cm), and the mAb is eluted with 50 mM sodium phosphate plus 250 mM NaCl (with a conductivity of 25 mS/cm) at pH 8.0.

The amounts of monoclonal antibodies binding to the substrate as well as the percent recovery are shown in Table 9. The substrate exhibits high recovery of monoclonal antibodies at short residence times.

TABLE 9

| Residence time (min) | Bound (mg/ml) | Recovery (%) |
|---|---|---|
| 3 | 37.3 | ~98 |
| 4 | 47.0 | ~95 |
| 6 | 68.3 | ~92 |

EXAMPLE 58

This example demonstrates monoclonal antibody binding and recovery at 10% breakthrough and a residence time of 3 minutes using substrates according to embodiments of the invention.

Solid substrates are prepared according to Examples 3, 4, 8, and 9. Each solid substrate sample is loaded into a separate column and used to treat a sample of biological material comprising monoclonal antibodies as described in Example 56.

The mAb dynamic binding capacity (DBC) at 10% breakthrough and 3 minutes residence time, along with the percent recovery for each substrate is shown in Table 10.

TABLE 10

| Ligand (ligand density) | DBC (mg/ml) | Recovery (%) |
|---|---|---|
| 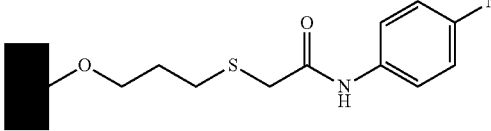 (78 μmol/ml) | 41 | >95 |
| 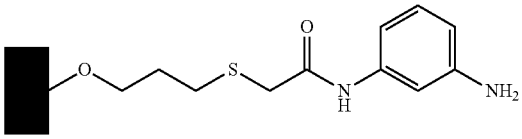 [SMILES: Nc1cccc(NC(=O)CSCCCOC2CCCCC2)c1] (68 μmol/ml) | 39 | >95 |
| 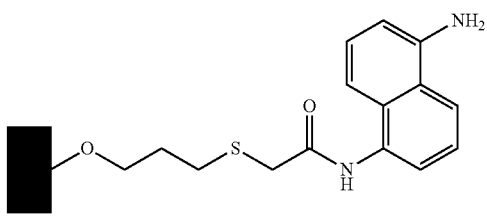 [SMILES: Nc1cccc2c(NC(=O)CSCCCOC3CCCCC3)cccc12] (41 μmol/ml) | 35 | 83 |

TABLE 10-continued

| Ligand (ligand density) | DBC (mg/ml) | Recovery (%) |
|---|---|---|
| [bead]—O—(CH$_2$)$_3$—S—CH$_2$—C(=O)—NH—(pyridine-NH$_2$) (58 μmol/ml) | 44.9 | >94 |

EXAMPLE 59

This example demonstrates aggregate removal using substrates according to embodiments of the invention.

Solid substrates are prepared according to Examples 4 and 5. Each solid substrate sample is loaded into a separate column and used to treat a sample of biological material comprising 75.5% monoclonal antibodies and 24.5% aggregates according to the procedure described in Example 56.

The amounts of monoclonal antibodies and aggregates in the samples after treatment with a substrate are shown in Table 11. After treatment with the substrate described in Example 3, the resulting product has 91.9% monoclonal antibodies and 8.1% aggregates. An even larger increase in the proportion of monoclonal antibodies compared to aggregates is observed for the sample treated with the substrate described in Example 3, which has 99.0% monoclonal antibodies and 1.0% aggregates after treatment.

EXAMPLE 60

This example demonstrates IgG static binding capacities using substrates according to embodiments of the invention.

Solid substrates are prepared according to Examples 3-12, 14, 15, and 19-45. The IgG static binding analysis is carried out by dissolving 27 mg of approximately 94% pure human lyophilized IgG (SeraCare Life Sciences, lot number G111RM-25B0802) in 10 ml of PBS to make 2.5 mg/ml IgG solution. A serial dilution of the IgG solution is prepared in duplicate, and the UV absorbance is determined at 280 nm. The absorbance values are used to plot a graph against the nominal concentrations, and the slope of this plot is used to calculate the actual IgG concentrations of the dilutions using 1.43 as the extinction coefficient of IgG. 50 μL of 1:1 slurry of each sample of beads in PBS is pipetted into separate 1.5 ml microcentrifuge tubes in duplicate, and 1 ml of 2.5 mg/ml IgG in PBS is added to each tube. Tubes are rotated for two hours

TABLE 11

| | mAb (%) | Aggregates (%) |
|---|---|---|
| Starting mAb material | 75.5 | 24.5 |
| Load at pH 7.4 and 15 mS/cm/ Elute at pH 4 [bead]—O—(CH$_2$)$_3$—S—CH$_2$—C(=O)—NH—(4-aminophenyl) | 91.9 | 8.1 |
| Load at pH 7.4 and 15 mS/cm/ Elute at pH 4 [bead]—O—(CH$_2$)$_3$—S—CH$_2$—C(=O)—NH—(3-aminophenyl) | 99.0 | 1.0 | and spun down for two minutes. 120 μL of each sample is then pipetted into 96-well plates, and the UV absorbance is read at 280 nm.
The static binding capacity and ligand density for each substrate are shown in Table 12. The substrates exhibit high static binding capacity even at low ligand densities.
TABLE 12
| Substrate | Ligand Density (μmol/ml) | Static Binding Capacity (mg/ml) |
|---|---|---|
| 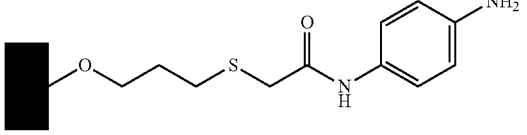 | 78 | 94 |
| 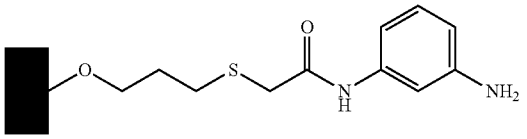 [SMILES: Nc1cccc(NC(=O)CSCCCOC2CCCCC2)c1] | 62 | 93 |
| 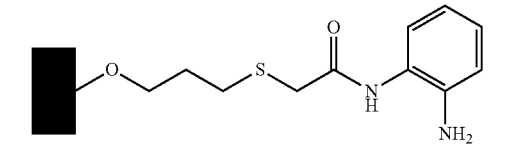 [SMILES: Nc1ccccc1NC(=O)CSCCCOC1CCCCC1] | 40 | 77 |
| 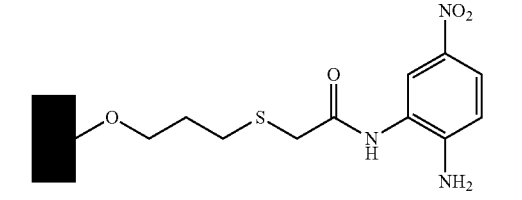 [SMILES: Nc1ccc([N+](=O)[O-])cc1NC(=O)CSCCCOC1CCCCC1] | ND | 92 |
| 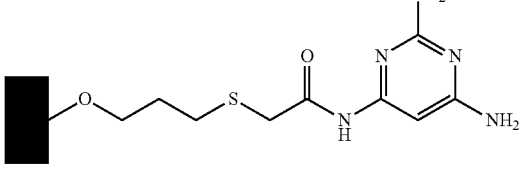 | 30 | 72 |
| 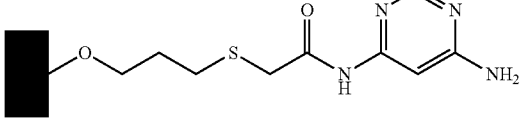 | 30 | 82 |
| 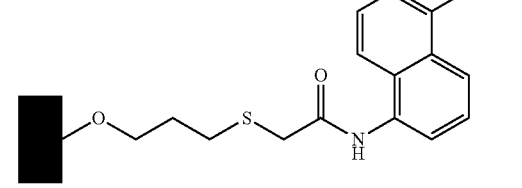 | 41 | 100 |
| 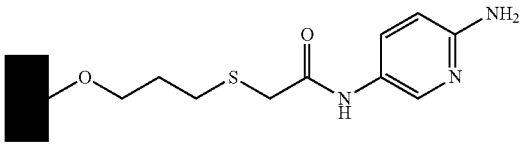 [SMILES: Nc1ccc(NC(=O)CSCCCOC2CCCCC2)cn1] | 58 | 95 |

TABLE 12-continued
| Substrate | Ligand Density (μmol/ml) | Static Binding Capacity (mg/ml) |
|---|---|---|
| 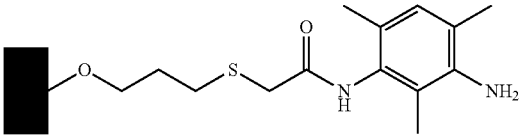 [SMILES: Cc1cc(C)c(NC(=O)CSCCCOC2CCCCC2)c(C)c1N] | 72 | 91 |
| 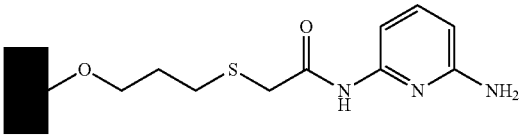 [SMILES: Nc1cccc(NC(=O)CSCCCOC2CCCCC2)n1] | 26 | 76 |
| 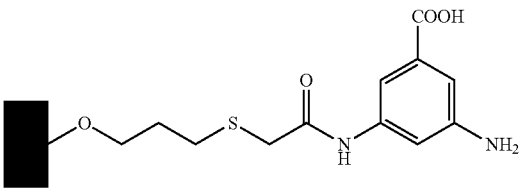 [SMILES: Nc1cc(NC(=O)CSCCCOC2CCCCC2)cc(C(=O)O)c1] | 30 | 58 |
| 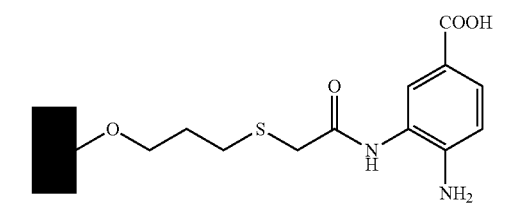 [SMILES: Nc1ccc(C(=O)O)cc1NC(=O)CSCCCOC1CCCCC1] | 70 | 100 |
| 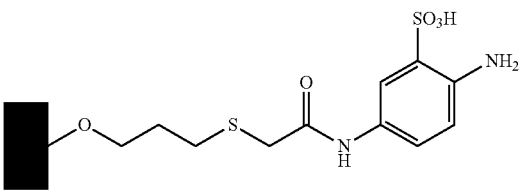 [SMILES: Nc1ccc(NC(=O)CSCCCOC2CCCCC2)cc1S(=O)(=O)O] | 28 | 51 |
| 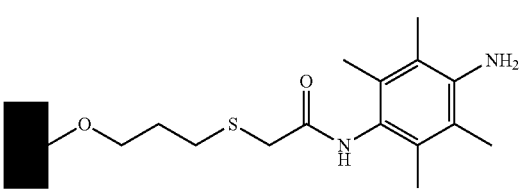 [SMILES: Cc1c(C)c(NC(=O)CSCCCOC2CCCCC2)c(C)c(C)c1N] | 65 | 98 |
| 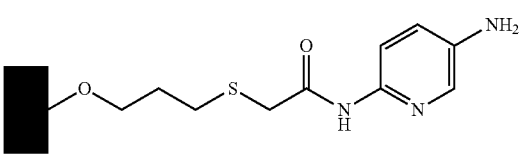 [SMILES: Nc1ccc(NC(=O)CSCCCOC2CCCCC2)nc1] | 54 | 40 |
| 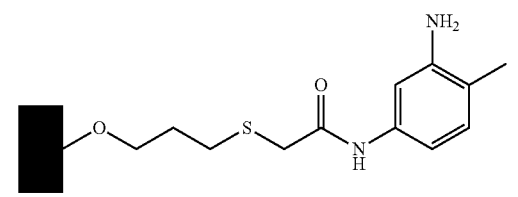 [SMILES: Cc1ccc(NC(=O)CSCCCOC2CCCCC2)cc1N] | 78 | 30 |

TABLE 12-continued
| Substrate | Ligand Density (μmol/ml) | Static Binding Capacity (mg/ml) |
|---|---|---|
| 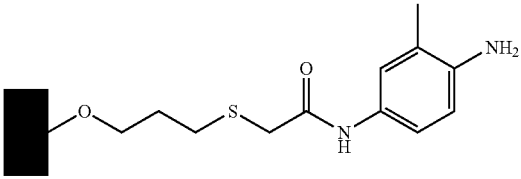 [SMILES: Cc1cc(NC(=O)CSCCCOC2CCCCC2)ccc1N] | 85 | 35 |
| 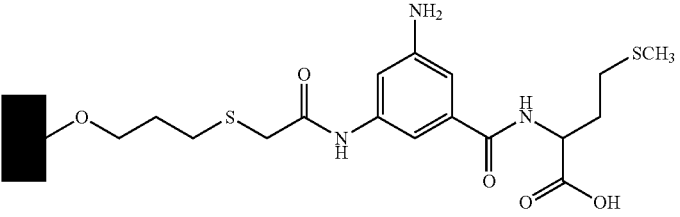 [SMILES: CSCCC(NC(=O)c1cc(N)cc(NC(=O)CSCCCOC2CCCCC2)c1)C(=O)O] | 61 | 70 |
| 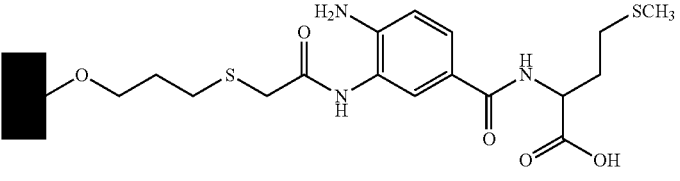 [SMILES: CSCCC(NC(=O)c1ccc(N)c(NC(=O)CSCCCOC2CCCCC2)c1)C(=O)O] | 103 | 88 |
| 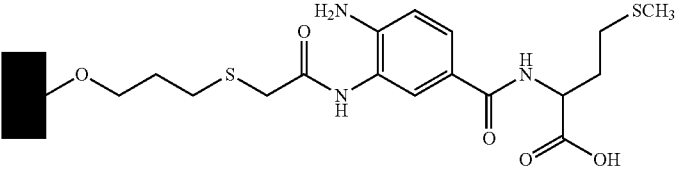 [SMILES: CSCCC(NC(=O)c1ccc(N)c(NC(=O)CSCCCOC2CCCCC2)c1)C(=O)O] | 64 | 75 |
| 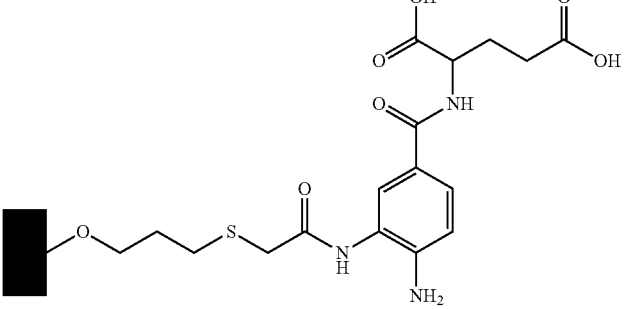 [SMILES: Nc1ccc(C(=O)NC(CCC(=O)O)C(=O)O)cc1NC(=O)CSCCCOC1CCCCC1] | 98 | 80 |
| 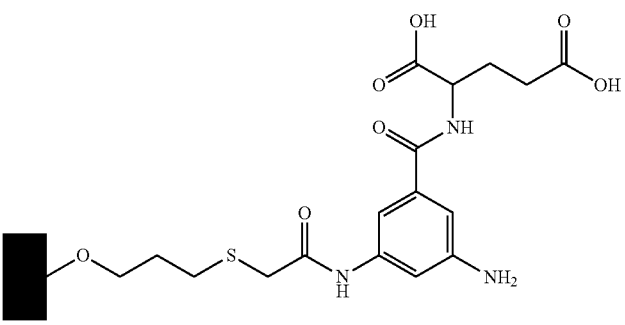 [SMILES: Nc1cc(NC(=O)CSCCCOC2CCCCC2)cc(C(=O)NC(CCC(=O)O)C(=O)O)c1] | 94 | 78 |

TABLE 12-continued

| Substrate | Ligand Density (μmol/ml) | Static Binding Capacity (mg/ml) |
|---|---|---|
| | 72 | 90 |
| | 62 | 95 |
| | 56 | 87 |
| | 60 | 40 |
| | 70 | 82 |
| | 134 | 90 |

US 8,802,448 B2
TABLE 12-continued
| Substrate | Ligand Density (μmol/ml) | Static Binding Capacity (mg/ml) |
|---|---|---|
| 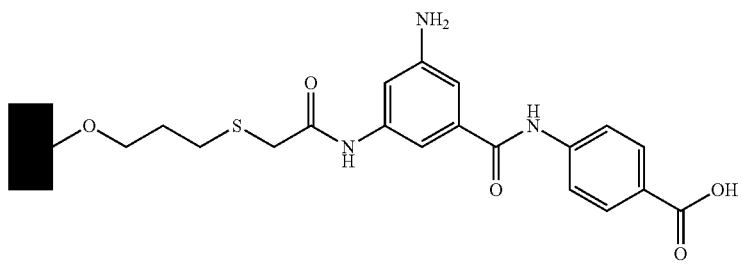 [SMILES: Nc1cc(NC(=O)CSCCCOC2CCCCC2)cc(C(=O)Nc2ccc(C(=O)O)cc2)c1] | 65 | 65 |
| 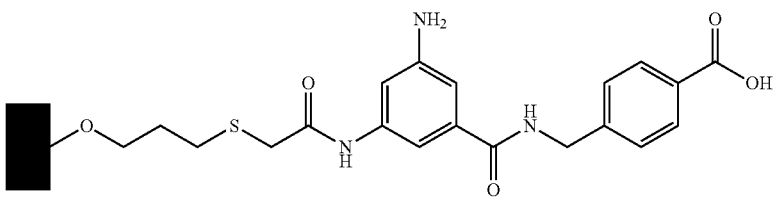 [SMILES: Nc1cc(NC(=O)CSCCCOC2CCCCC2)cc(C(=O)NCc2ccc(C(=O)O)cc2)c1] | 49 | 55 |
| 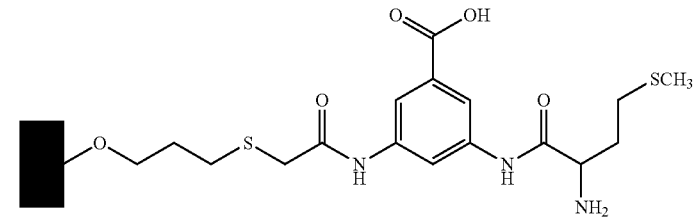 [SMILES: CSCCC(N)C(=O)Nc1cc(NC(=O)CSCCCOC2CCCCC2)cc(C(=O)O)c1] | 55 | 60 |
| 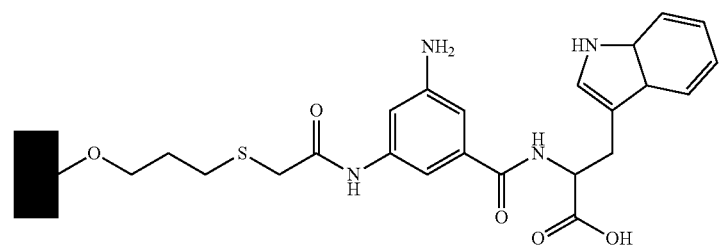 [SMILES: Nc1cc(NC(=O)CSCCCOC2CCCCC2)cc(C(=O)NC(CC2=CNC3C=CC=CC23)C(=O)O)c1] | 110 | 95 |
| 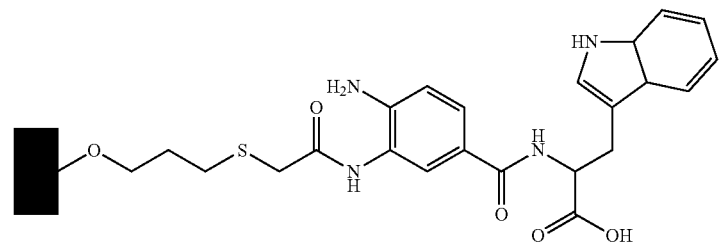 [SMILES: Nc1ccc(C(=O)NC(CC2=CNC3C=CC=CC23)C(=O)O)cc1NC(=O)CSCCCOC1CCCCC1] | 72 | 74 |
| 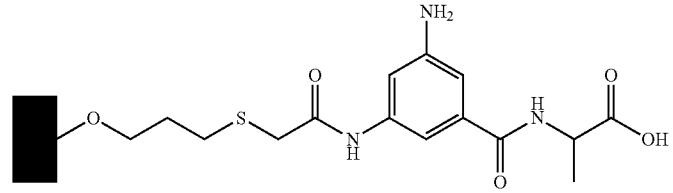 | 64 | 78 |

TABLE 12-continued

| Substrate | Ligand Density (µmol/ml) | Static Binding Capacity (mg/ml) |
|---|---|---|
|  | 68 | 72 |
|  | 55 | 48 |
|  | 92 | 85 |
|  | 46 | 60 |
|  | 65 | 82 |
|  | 61 | 76 |

EXAMPLE 61

This example demonstrates BSA (bovine serum albumin) static binding capacities using substrates according to embodiments of the invention.

Solid substrates are prepared according to Examples 22-26, 29-31, 34, 35, 37, 38, 41, 42, and 44. The BSA static binding analysis is carried out by dissolving 22 mg of approximately 96% pure BSA powder (Sigma Aldrich, batch number 106K0687) in 10 ml of 0.1M MES at pH 4.7 to make a 2 mg/ml BSA solution. A serial dilution of the BSA solution is prepared in duplicate, and the UV absorbance is determined at 280 nm. The absorbance values are used to plot a graph against the nominal concentrations, and the slope of this plot is used to calculate the actual BSA concentrations of the dilutions using 0.625 as the extinction coefficient of BSA. 50 µL of 1:1 slurry of each sample of beads in 0.1M MES pH 4.7 is pipetted into separate 1.5 ml microcentrifuge tubes in duplicate, and 1 ml of 2 mg/ml BSA in 0.1M MES pH 4.7 is added to each tube. Tubes are rotated for two hours and spun down for two minutes. 120 µL of each sample is then pipetted into 96-well plates, and the UV absorbance is read at 280 nm.

The static binding capacity and ligand density for each substrate are shown in Table 13. The substrates exhibit high static binding capacity even at low ligand densities.

TABLE 13

| Substrate | Ligand Density (µmol/ml) | Static Binding Capacity (mg/ml) |
|---|---|---|
| (structure 1) | 78 | 5 |
| (structure 2) | 85 | 5 |
| (structure 3) | 61 | 45 |
| (structure 4) | 103<br>64 | 65<br>45 |
| (structure 5) | 98 | 50 |

TABLE 13-continued
| Substrate | Ligand Density (μmol/ml) | Static Binding Capacity (mg/ml) |
| --- | --- | --- |
| 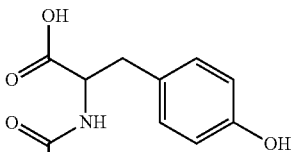 | 62 | 72 |
| 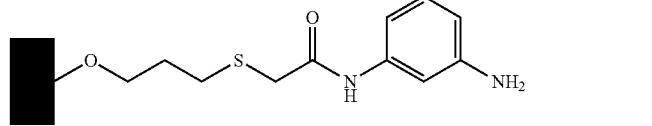 | 56 | 60 |
| 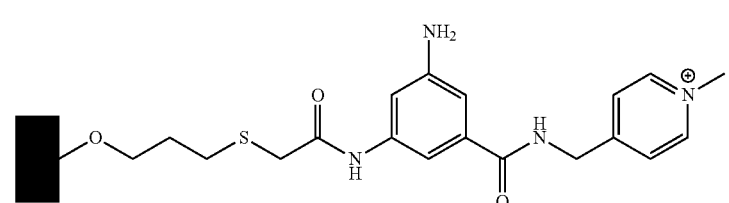 [SMILES: C[n+]1ccc(CNC(=O)c2cc(N)cc(NC(=O)CSCCCOC3CCCCC3)c2)cc1] | 60 | 50 |
| 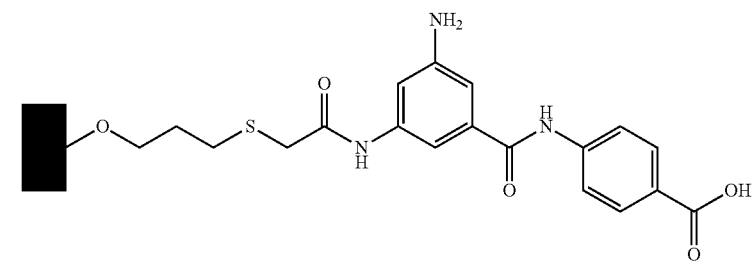 [SMILES: Nc1cc(NC(=O)CSCCCOC2CCCCC2)cc(C(=O)Nc2ccc(C(=O)O)cc2)c1] | 65 | 54 |
| 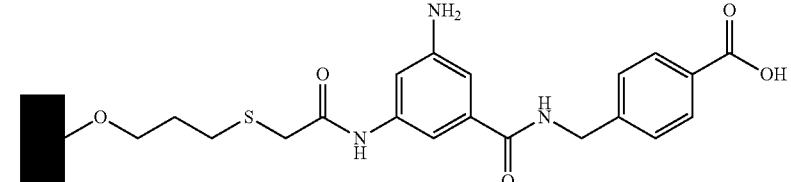 | 49 | 35 |
| 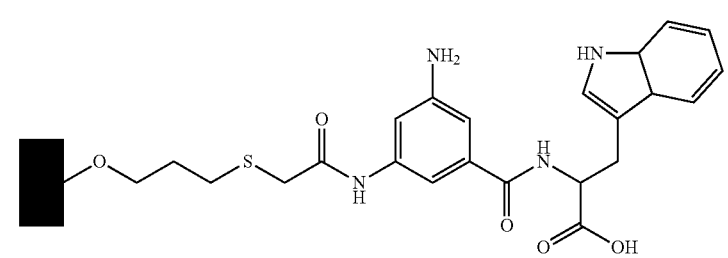 [SMILES: Nc1cc(NC(=O)CSCCCOC2CCCCC2)cc(C(=O)NC(CC2=CNC3C=CC=CC23)C(=O)O)c1] | 110 | 75 |

TABLE 13-continued

| Substrate | Ligand Density (μmol/ml) | Static Binding Capacity (mg/ml) |
|---|---|---|
| 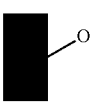 | 72 | 50 |
| 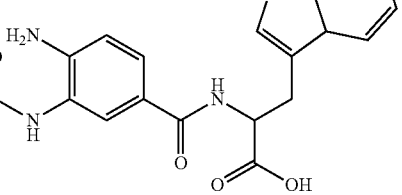 | 55 | 55 |
| 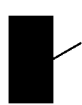 | 92 | 50 |
| 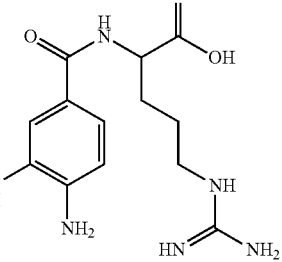 | 65 | 35 |

EXAMPLE 62

This example demonstrates the effect of pH and conductivity values on pure bovine serum albumin (BSA) dynamic binding at 10% breakthrough using substrates according to embodiments of the invention.

Figure 3:
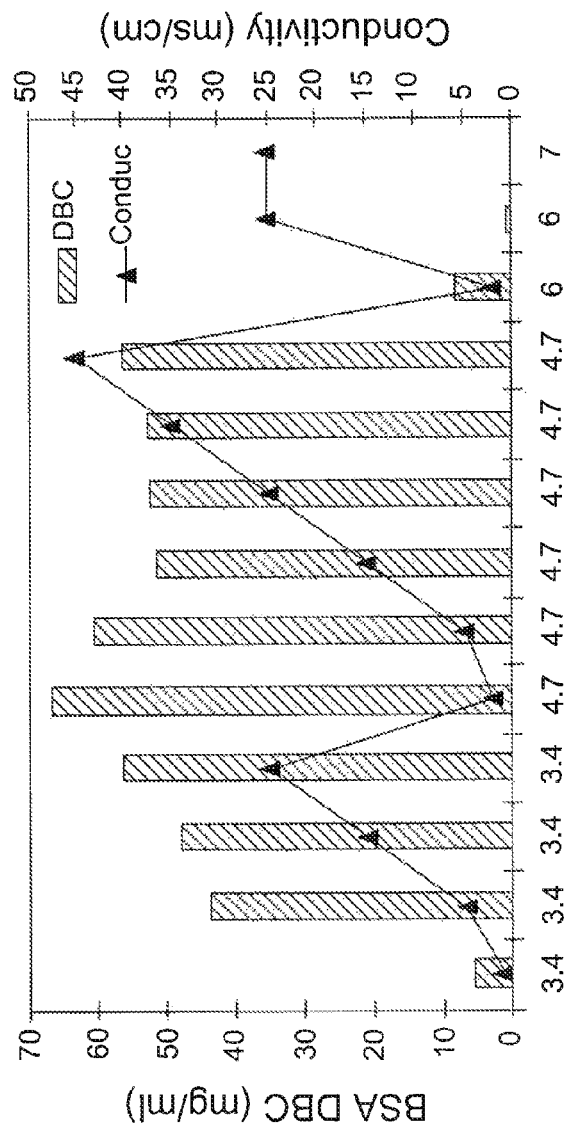
FIG. 3 is a graph showing the effect of pH and conductivity values on pure BSA (bovine serum albumin) dynamic binding capacity (DBC) at 10% breakthrough using a substrate according to an embodiment of the invention.

A solid substrate is prepared according to Example 20. Each solid substrate sample is loaded into a separate column and used to determine the dynamic binding capacity (DBC) of BSA according to the following procedure: BSA 2 mg/ml in various buffer solutions with variable pH (3.4-8.5) and variable conductivity (0-80 mS/cm) is loaded onto each column until the 10% breakthrough is reached (FIG. 3). The column is then washed with the loading buffer (e.g, pH 4.7 and a conductivity of 15 mS/cm) to remove BSA adsorbed to the substrate. The BSA is then eluted using 50 mM sodium phosphate buffer at pH 8.0 and 250 mM NaCl.

The amount of BSA bound at 10% breakthrough for each tested pH and conductivity combination is shown in FIG. 3. At pH values greater than or equal to 6.0, no BSA binding was observed at conductivity higher than 5 mS/cm. At pH 3.4, the BSA binding capacity increases with the increase in conductivity. For this ligand, pH 4.7 is the optimum loading pH, with a conductivity less than or equal to 15 mS/cm.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A substrate having a formula selected from the group consisting of:

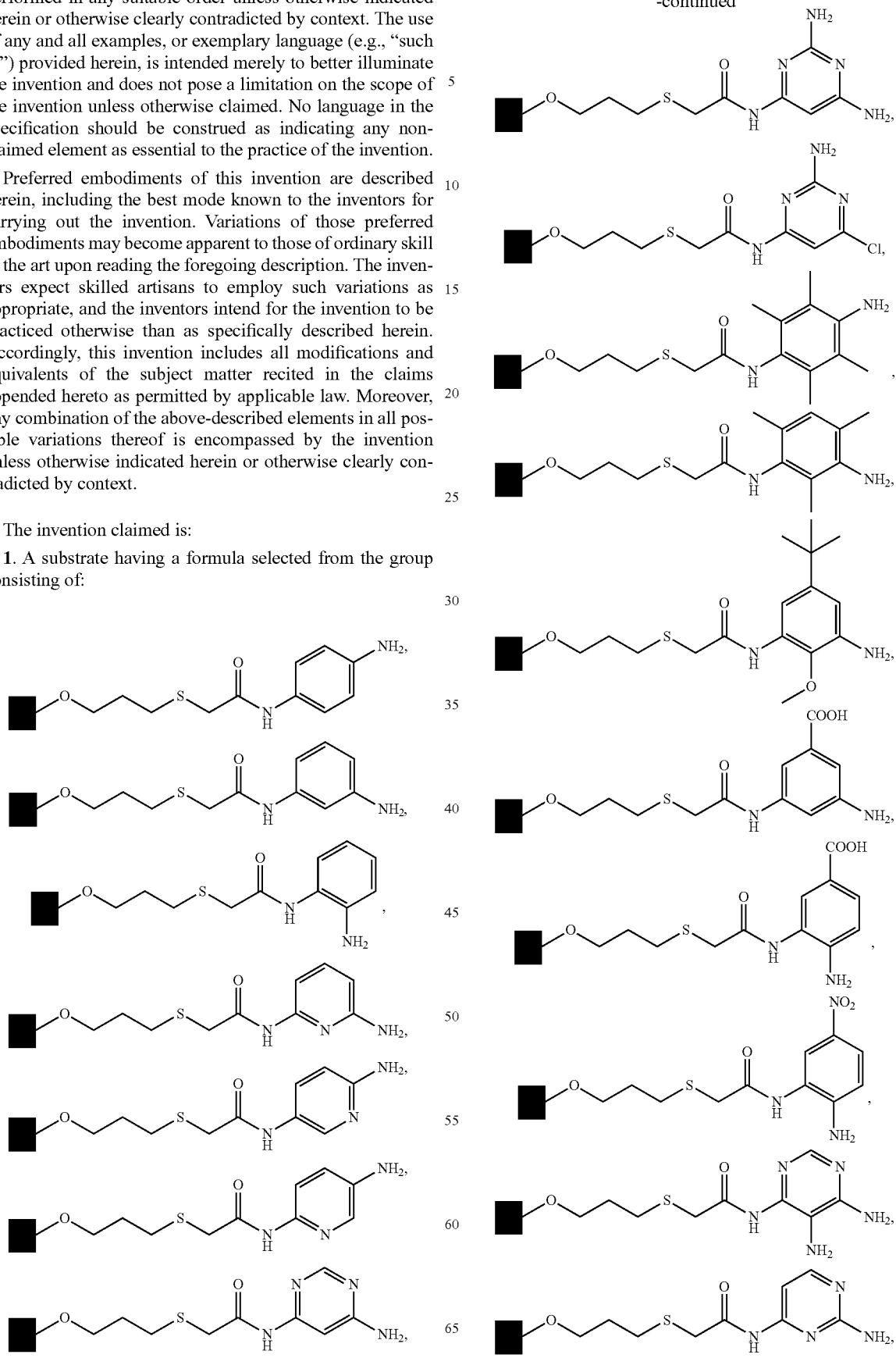

93
-continued
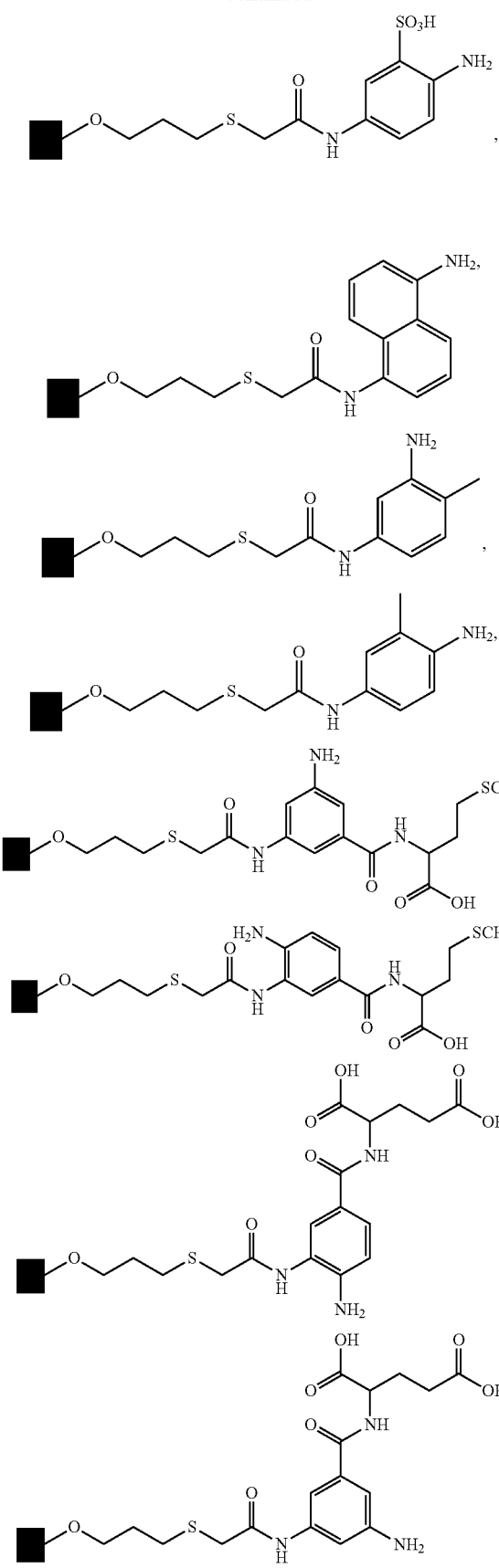
94
-continued
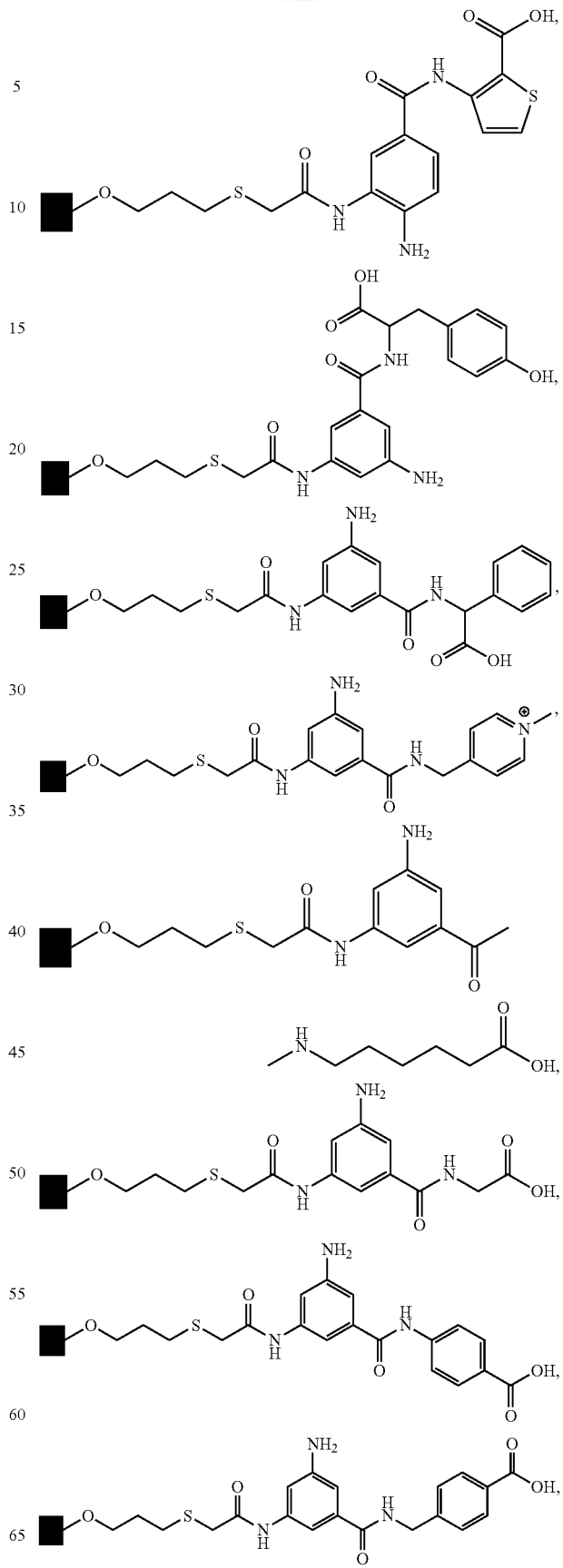

-continued

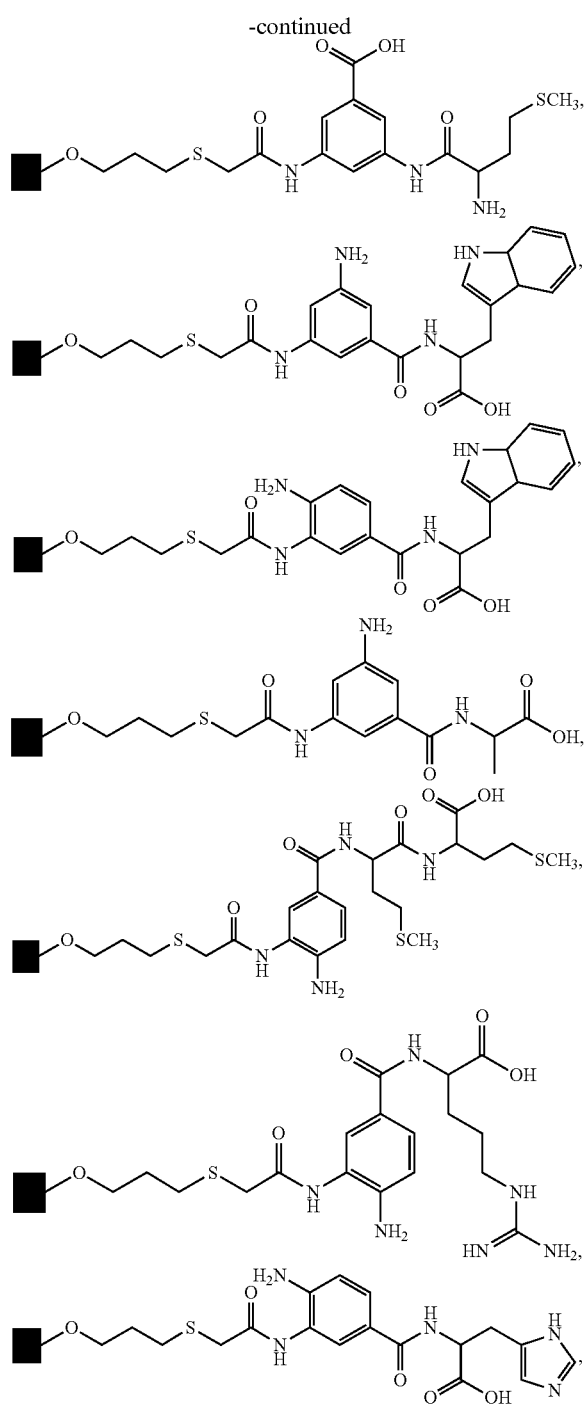

-continued

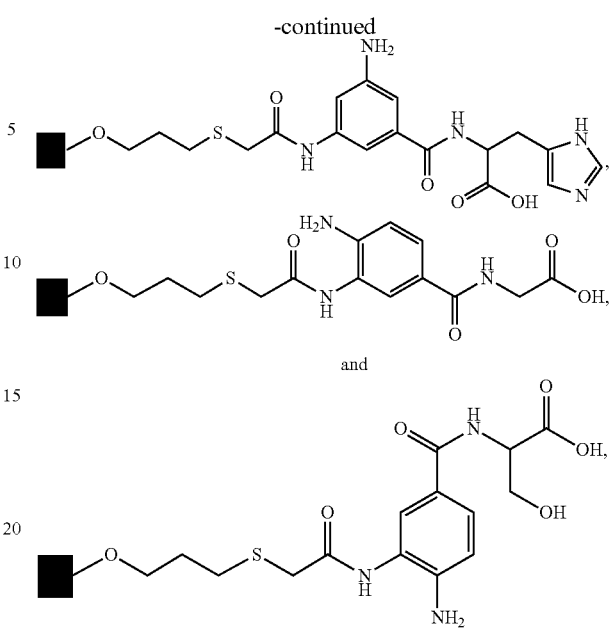

wherein the black rectangle represents a solid support.

2. A method of treating a sample comprising at least one biological substance with a substrate of claim 1, the method comprising contacting the substrate with the sample for a period of time sufficient to allow at least one biological substance in the sample to bind to the substrate.

3. A method for separating at least one substance from a liquid sample, the method comprising contacting the substrate according to claim 1 with a liquid sample comprising the at least one substance, wherein the substance adsorbs to the substrate; and, adjusting the pH, ionic strength, or both, such that the substance desorbs from the substrate.

4. The method of claim 3, wherein the at least one substance comprises an antibody.

5. The method of claim 3, comprising selectively binding IgG, IgM and/or IgA.

6. The method of claim 3, wherein the at least one substance comprises an antibody fragment.

7. The method of claim 3, wherein the sample comprises a biological fluid.

8. The method of claim 7, wherein sample comprises plasma.

9. The method of claim 3, wherein the substrate is disposed in a column, and the method comprises passing the sample through the column.

* * * * *